US012758260B2

(12) United States Patent
Tierney et al.

(10) Patent No.: US 12,758,260 B2
(45) Date of Patent: Oct. 13, 2026

(54) BONE-PENETRATING INTRAOSSEOUS ACCESS DEVICE

(71) Applicant: Teleflex Life Sciences II LLC, Wilmington, DE (US)

(72) Inventors: Morgan Tierney, Ferbane (IE); Aleksejus Fominas, Athlone (IE); Wade Kevin Trexler, Coopersburg, PA (US); Kurt Donald Heinly, Wernersville, PA (US); David Troy Rowe, Fleetwood, PA (US); Stephan M. Huhn, Manheim, PA (US)

(73) Assignee: TELEFLEX LIFE SCIENCES II LLC, Wilmington, DE (US)

( * ) Notice: Subject to any disclaimer, the term of this patent is extended or adjusted under 35 U.S.C. 154(b) by 618 days.

(21) Appl. No.: 17/555,210

(22) Filed: Dec. 17, 2021

(65) Prior Publication Data

US 2022/0104849 A1 Apr. 7, 2022

Related U.S. Application Data

(63) Continuation of application No. PCT/IB2020/055745, filed on Jun. 18, 2020.
(Continued)

(51) Int. Cl.
*A61B 17/34* (2006.01)
*A61B 17/00* (2006.01)

(52) U.S. Cl.
CPC ...... *A61B 17/3472* (2013.01); *A61B 17/3423* (2013.01); *A61B 17/3496* (2013.01);
(Continued)

(58) Field of Classification Search
CPC ............ A61B 17/3472; A61B 17/3423; A61B 17/3496; A61B 2017/00424;
(Continued)

(56) References Cited

U.S. PATENT DOCUMENTS

2008/0009894 A1 1/2008 Smith
2008/0208136 A1 8/2008 Findlay et al.
(Continued)

FOREIGN PATENT DOCUMENTS

CN 101325914 A 12/2008
CN 101917913 A 12/2010
(Continued)

OTHER PUBLICATIONS

International Search Report for International application No. PCT/IB2020/055745, mailed Dec. 10, 2020.

*Primary Examiner* — Tan-Uyen T Ho
*Assistant Examiner* — Bridget E. Rabaglia
(74) *Attorney, Agent, or Firm* — BakerHostetler

(57) ABSTRACT

An intraosseous access device is operable to provide access to a sternal intraosseous space in a first mode of operation and operable to provide access to a peripheral intraosseous space in a second mode of operation. The device includes an outer sleeve, an inner penetrator hub, and an outer penetrator hub. A protective shield is telescopically coupled to the outer sleeve. The protective shield is operable to move from an expanded position to a retracted position in both the first and second modes of operation. A bone probe ring is disposed within the protective shield and configured to move between an extended position and a retracted position in both the first and second modes of operation. An actuator is operable to manually move the protective shield and the bone probe ring to the retracted position when in the second mode of operation.

15 Claims, 25 Drawing Sheets

Related U.S. Application Data

(60) Provisional application No. 62/865,177, filed on Jun. 22, 2019.

(52) U.S. Cl.
CPC ............... *A61B 2017/00424* (2013.01); *A61B 2017/3407* (2013.01)

(58) Field of Classification Search
CPC .... A61B 2017/3407; A61B 2090/0801; A61B 10/025; A61B 17/1671; A61B 2010/0258; A61B 17/8805; A61B 17/3476; A61B 17/8819; A61B 2010/0208; A61B 17/34; A61B 18/1477; A61B 17/3478; A61B 17/3401; A61B 5/150389; A61B 2017/348
See application file for complete search history.

(56) References Cited

U.S. PATENT DOCUMENTS

| | | | | |
|---|---|---|---|---|
| 2013/0041345 | A1 | 2/2013 | Kilcoin et al. | |
| 2013/0267785 | A1 | 10/2013 | Sutherland et al. | |
| 2017/0105763 | A1 | 4/2017 | Karve et al. | |
| 2017/0181734 | A1 * | 6/2017 | Tzachar ............. | A61M 5/3287 |
| 2018/0236182 | A1 | 8/2018 | Charlebois et al. | |
| 2018/0256209 | A1 | 9/2018 | Muse et al. | |

FOREIGN PATENT DOCUMENTS

| | | | |
|---|---|---|---|
| CN | 103328022 | A | 9/2013 |
| CN | 104302334 | A | 1/2015 |
| CN | 108348740 | A | 7/2018 |
| WO | 2009070896 | A1 | 6/2009 |
| WO | 2012/103428 | A2 | 8/2012 |
| WO | 2019215705 | A1 | 11/2019 |

* cited by examiner

BONE-PENETRATING INTRAOSSEOUS ACCESS DEVICE

CROSS-REFERENCE TO RELATED APPLICATIONS

The present application is a Continuation of International Application No. PCT/IB2020/055745, filed Jun. 18, 2020, which claims the benefit of priority to U.S. Provisional Patent Application No. 62/865,177, filed Jun. 22, 2019, the contents of which are incorporated herein in their entirety.

TECHNICAL FIELD

The present disclosure generally relates to a medical apparatus for locating and accessing an intraosseous space of a patient. More specifically, the present disclosure relates to a bone-penetrating intraosseous access device for placement of a conduit into the intraosseous space within a bone of a patient.

BACKGROUND

Many life-threatening emergencies, including shock, trauma, cardiac arrest, drug overdoses, diabetic ketoacidosis, arrhythmias, burns, and status epilepticus, just to name a few, often unnecessarily result in death because intravenous (IV) access cannot be achieved in a timely manner. An essential element for treating many life threatening emergencies is the rapid establishment of an IV line in order to administer drugs and fluids directly into a patient's vascular system. Whether in an ambulance by paramedics, in an emergency room by emergency specialists or on a battlefield by an Army medic, the goal is the same—quickly start an IV in order to administer lifesaving drugs and fluids. To a large degree, ability to successfully treat most critical emergencies is dependent on the skill and luck of an operator in accomplishing vascular access. While relatively easy to start an IV on some patients, doctors, nurses and paramedics may nevertheless experience difficulty establishing IV access in some patients. The success rate on the battlefield may be much lower, in which wounded soldiers are often probed repeatedly with sharp needles in an attempt to quickly establish IV access.

In the case of patients with chronic disease or the elderly, availability of easily accessible veins may be depleted. Other patients may have no available IV sites due to anatomical scarcity of peripheral veins, obesity, extreme dehydration or previous IV drug use. For such patients, finding a suitable site for administering lifesaving therapy often becomes a monumental and frustrating task. As a result, patients with life threatening emergencies may die when access to the vascular system with lifesaving IV therapy is delayed or simply not possible.

There are various circumstances under which it is desirable to introduce drugs or other liquids into the marrow of a subject's bone. For example, in cases where a subject has suffered from serious trauma or cardiac arrest it may not be practical to deliver liquids by way of intravenous (IV) infusions. Intraosseous infusion may also be useful for delivering fluids to newborns and small children in which suitable blood vessels are difficult to access. Intraosseous infusion may be used to deliver fluids into a subject's sternum, humerus, femur, tibia, or other bone. Intraosseous infusion has the advantage that, with appropriate technology, a pathway for intraosseous infusion can be established very rapidly. This can save lives in critical situations. Portals in bone may also be applied to withdraw or aspirate fluid from within the bone.

The intraosseous (IO) space provides a direct conduit to a patient's vascular system and provides an attractive alternate route to administer IV drugs and fluids. Drugs administered intraosseously enter a patient's blood circulation system rapidly, thus bone marrow may function as a large non-collapsible vein.

Proper placement of an intraosseous needle in the bone is critical. If a user attempts to insert the needle in the wrong place, the bone might be too thick and therefore difficult for the needle to penetrate. Alternatively, the bone might be too thin, in which case the needle could completely penetrate the anterior and posterior sides of the bone, thus missing the intraosseous region entirely. Also, placing the needle at an angle that is not substantially perpendicular to the surface of the bone may lead to the needle breaking, or other complications. Furthermore, certain powered drivers are unable to successfully penetrate bone when their respective power source is depleted. Additionally, the sharp penetrator tips of conventional driver assemblies can be dangerous if they are accidentally mishandled by a user prior to a planned insertion procedure. For instance, without adequate sharps protection, the user is susceptible to accidentally poking himself or another individual with the penetrator.

Therefore, a need exists for a bone-penetrating manual driver and stabilizer assembly operable to locate a suitable insertion site and provide a quick and easy conduit to an intraosseous space within a bone of a patient. There is a further need for a bone-penetrating manual driver and stabilizer assembly having a first mode of operation for sternal insertion, and a second mode of operation for peripheral insertion.

SUMMARY

The foregoing needs are met by implementations of an apparatus for accessing an intraosseous space within a bone of a patient according to the present disclosure. According to one aspect of the disclosure, the apparatus comprises an intraosseous access device comprising a penetrator assembly having a sharp penetrating end operable to penetrate a bone and associated bone marrow; a housing having an internal cavity and an outer sleeve, the outer sleeve defining a handle operable to manually drive the penetrator assembly into the bone and associated bone marrow; a retainer having a distal retainer end and a proximal retainer end, the retainer slidably coupled to the outer sleeve; and a protective shield having a distal shield end, a proximal shield end, and a longitudinal hollow passageway extending between the distal shield end and the proximal shield end, the protective shield slidably coupled to the outer sleeve; where the penetrator assembly is operable to provide intraosseous access at a sternal insertion site when the intraosseous access device is in a first mode of operation; and where the penetrator assembly is operable to provide intraosseous access at a peripheral insertion site when the intraosseous access device is in a second mode of operation.

According to another aspect of the disclosure, the penetrator assembly further comprises an inner penetrator hub having a distal end and a proximal end, an inner penetrator extending from the distal end of the inner penetrator hub, an outer penetrator hub having a distal end and a proximal end, and an outer penetrator extending from the distal end of the outer penetrator hub, the outer penetrator defining a longitudinal hollow bore configured to slidably receive the inner penetrator.

According to another aspect of the disclosure, the proximal end of the outer penetrator hub is releasably engaged to the distal end of the inner penetrator hub.

According to another aspect of the disclosure, a housing core is fixedly disposed within the internal cavity of the housing, the housing core including a distal core end coupled to the proximal end of the inner penetrator hub.

According to another aspect of the disclosure, the inner penetrator comprises a rigid stylet, and the outer penetrator comprises a flexible cannula.

According to another aspect of the disclosure, the handle includes an ergonomic grip suitable for grasping during the first and second modes of operation.

According to another aspect of the disclosure, the handle is configured to allow manual force to be applied and at the same time permit rotation of the handle to rotate the penetrator assembly during intraosseous insertion of the penetrator assembly during the first and second modes of operation.

According to another aspect of the disclosure, the protective shield is configured to move between an extended position and a retracted position relative to the outer sleeve and the retainer during the first mode of operation.

According to another aspect of the disclosure, the protective shield is configured to provide sharps protection from the sharp penetrating end of the penetrator assembly when the protective shield is in the extended position during the first mode of operation, and wherein the protective shield is configured to expose the sharp penetrating end of the penetrator assembly when the protective shield is in the retracted position to permit insertion of the penetrator assembly into the bone and associated bone marrow during the first mode of operation.

According to another aspect of the disclosure, a first biasing member is disposed between the retainer and the protective shield, the first biasing member configured to bias the protective shield toward the extended position during the first mode of operation.

According to another aspect of the disclosure, the first biasing member comprises a compression spring.

According to another aspect of the disclosure, a bone probe ring is slidably coupled to the retainer, the bone probe ring having a distal ring end and a proximal ring end.

According to another aspect of the disclosure, a bone probe extends from the distal ring end of the bone probe ring, the bone probe including a bone probe tip operable to penetrate skin and subcutaneous tissue.

According to another aspect of the disclosure, the bone probe tip of the bone probe is disposed within the longitudinal passageway of the protective shield to provide sharps protection when the protective shield is in the extended position during the first mode of operation, and wherein the bone probe tip of the bone probe extends from the longitudinal passageway of the protective shield when the protective shield is in the retracted position during the first mode of operation.

According to another aspect of the disclosure, the bone probe ring is configured to move between a first position and a second position during the first mode of operation, where the bone probe ring is closer to the distal retainer end of the retainer when the bone probe ring is in the first position than when the bone probe ring is in the second position.

According to another aspect of the disclosure, the distal ring end of the bone probe ring includes an inwardly protruding nub, the nub configured to engage a first detent on the retainer to maintain the bone probe ring in the first position during the first mode of operation, and the nub configured to engage a second detent on the retainer to maintain the bone probe ring in the second position during the first mode of operation.

According to another aspect of the disclosure, the nub is operable to snap into the second detent on the retainer.

According to another aspect of the disclosure, a feedback is provided to a user when the nub is snapped into the second detent on the retainer.

According to another aspect of the disclosure, the feedback comprises at least one of an audible response and a tactile response to indicate insertion of the penetrator assembly into the intraosseous space.

According to another aspect of the disclosure, a second biasing member is disposed between the retainer and the bone probe ring, the second biasing member configured to bias the bone probe ring toward the first position during the first mode of operation.

According to another aspect of the disclosure, the second biasing member comprises a compression spring.

According to another aspect of the disclosure, a stabilizer base is releasably connected to the distal shield end of the protective shield.

According to another aspect of the disclosure, the stabilizer base includes an alignment cutout configured to align with a sternal notch of a patient to indicate proper placement of the intraosseous access device at the sternal insertion site during the first mode of operation.

According to another aspect of the disclosure, the stabilizer base further comprises a guide hole configured to guide the penetrator assembly during the first mode of operation.

According to another aspect of the disclosure, the outer sleeve further comprises a longitudinal track and a slider slidably coupled to the longitudinal track, the slider operable to move the retainer and the protective shield between a deployed position and an undeployed position relative to the outer sleeve during the second mode of operation.

According to another aspect of the disclosure, the protective shield is configured to provide sharps protection from the sharp penetrating end of the penetrator assembly when the protective shield is in the deployed position during the second mode of operation; and wherein the protective shield is configured to expose the sharp penetrating end of the penetrator assembly when the protective shield is in the undeployed position to permit insertion of the penetrator assembly into the bone and associated bone marrow during the second mode of operation.

According to another aspect of the disclosure, the slider is configured to move between an engaged position with the housing core and a disengaged position with the housing core, wherein the slider is prevented from moving along the longitudinal track when in the engaged position, and wherein the slider is permitted to move along the longitudinal track when in the disengaged position.

According to another aspect of the disclosure, the outer sleeve further comprises a slide lock operable to move between a locked position with the slider and an unlocked position with the slider, the slide lock configured to secure the slider in the engaged position with the housing core when the slide lock is in the locked position.

According to another aspect of the disclosure, further comprising a removable safety latch removably attachable to the outer sleeve and configured to prevent the activation of the slider when the safety latch is attached to the outer sleeve.

According to another aspect of the disclosure, wherein the outer sleeve further comprises a safety push button operable to prevent the protective shield from retracting into the outer sleeve during the first and second modes of operation when the safety push button is activated.

According to another aspect of the disclosure, a method of accessing an intraosseous space of a patient comprises: providing an intraosseous access device comprising a penetrator assembly having a sharp penetrating end operable to penetrate a bone and associated bone marrow, a housing having an internal cavity and an outer sleeve defining a handle, a retainer slidably coupled to the outer sleeve, a protective shield slidably coupled to the outer sleeve, and a stabilizer base coupled to the protective sleeve; determining a mode of operation of the intraosseous access device based on a location of a target site for intraosseous access; positioning the stabilizer over a patient's sternum and manually driving the penetrator assembly into a sternal intraosseous space when the mode of operation is a first mode of operation; and manually retracting the protective shield and the retainer relative to the outer sleeve and manually driving the penetrator assembly into a peripheral intraosseous space when the mode of operation is a second mode of operation.

According to another aspect of the disclosure, the penetrator assembly comprises an inner penetrator hub having a distal end and a proximal end, an inner penetrator extending from the distal end of the inner penetrator hub, an outer penetrator hub having a distal end and a proximal end, and an outer penetrator extending from the distal end of the outer penetrator hub, the outer penetrator defining a longitudinal hollow bore configured to slidably receive the inner penetrator.

According to another aspect of the disclosure, the method further comprises moving the protective shield from an extended position to a retracted position relative to the outer sleeve and the retainer during the first mode of operation.

According to another aspect of the disclosure, the method further comprises inserting a bone probe into the patient proximate the insertion site during the first mode of operation until a tip of the bone probe contacts the bone.

According to another aspect of the disclosure, the method further comprises detaching the stabilizer base from the protective shield and removing the outer penetrator hub from the inner penetrator hub when the outer penetrator has accessed the intraosseous space during the first mode of operation.

There has thus been outlined certain aspects of the disclosure in order that the detailed description thereof may be better understood, and in order that the present contribution to the art may be better appreciated. There are additional implementations of the disclosure that will be described below and which form the subject matter of the claims appended hereto.

In this respect, before explaining at least one aspect of the intraosseous access device in detail, it is to be understood that the apparatus is not limited in its application to the details of construction and to the arrangements of the components set forth in the following description or illustrated in the drawings. The intraosseous access device is capable of aspects in addition to those described, and of being practiced and carried out in various ways. Also, it is to be understood that the phraseology and terminology employed herein, as well as the abstract, are for the purpose of description and should not be regarded as limiting.

As such, those skilled in the art will appreciate that the conception upon which this disclosure is based may readily be utilized as a basis for the designing of other structures, methods, and systems for carrying out the several purposes of the intraosseous access device. It is important, therefore, that the claims be regarded as including such equivalent constructions insofar as they do not depart from the spirit and scope of the disclosure.

BRIEF DESCRIPTION OF THE DRAWINGS

In order that the disclosure may be readily understood, aspects of the intraosseous (IO) access device are illustrated by way of examples in the accompanying drawings, in which like parts are referred to with like reference numerals throughout.

DETAILED DESCRIPTION

The present disclosure provides a bone-penetrating manual driver and stabilizer assembly operable to locate a suitable insertion site and penetrate the underlying bone, such as a human patient's sternum or a peripheral insertion site, to provide a quick and easy conduit to an intraosseous space within the bone for associated medical procedures, including delivery of fluid and medication, aspiration, and biopsy of bone marrow, among others.

Figure 1:
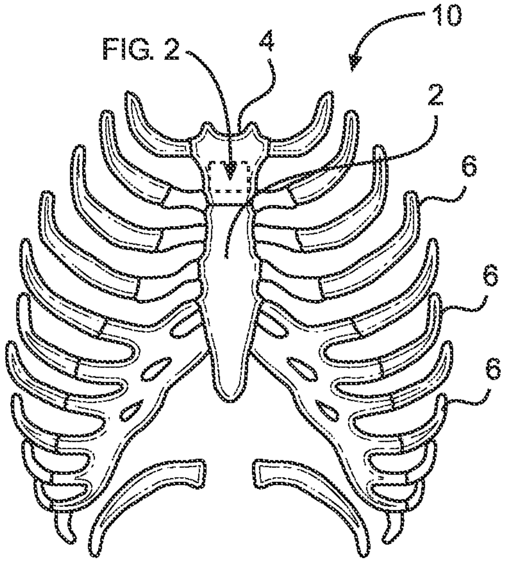
FIG. 1 illustrates a schematic view of a ribcage of a human.

FIG. 1 depicts a schematic view of the ribcage of a human 10. The sternum 2 is a flat, narrow bone between the ribs 6 comprising three segments: the manubrium, the body, and the xiphoid process. The sternum also comprises a sternal notch 4 (also called the "suprasternal notch" or the "jugular notch"), which is a U-shaped anatomical feature located above the sternum, below the throat, and between the clavicles.

Figure 2:
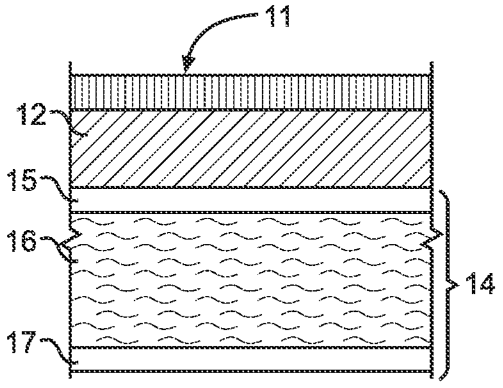
FIG. 2 illustrates a cross-sectional view of a region of the sternum of a human.

FIG. 2 shows a cross-sectional view of a portion of the sternum 2. Skin 11 overlays a layer of subcutaneous tissue 12, which in turn overlays bone 14. Bone 14 includes an intraosseous space 16 bounded by anterior compact bone (i.e., anterior cortex) 15 and posterior compact bone (i.e., posterior cortex) 17. Intraosseous space 16 is the region between the anterior cortex and the posterior cortex. Bone marrow includes blood, blood forming cells, and connective tissue found in the intraosseous space. Anterior compact bone 15 and posterior compact bone 17 are each approximately 2.0 millimeters (mm) thick and intraosseous space 16 is approximately 10.0 mm thick in most adult patients. Thus, the total thickness of bone 14 is approximately 14.0 mm in most adult patients. The target zone within the intraosseous space 16 is the center, which is approximately 7.0 mm from the upper surface of anterior compact bone 15 in most adult patients.

The intraosseous space 16 may be accessed by an intraosseous (10) access device, which may include, but is not limited to, a penetrator assembly comprising a hollow needle, hollow drill bit, bone penetrator, catheter, cannula, trocar, stylet, inner penetrator, outer penetrator, needle or needle set, or other device operable to provide access to an intraosseous space or interior portions of a bone. Such intraosseous access devices may be formed, at least in part, from metal alloys such as 304 stainless steel and other biocompatible materials associated with needles and similar medical devices. A wide variety of intraosseous access devices may be formed in accordance with one or more teachings of the present disclosure. For instance, trocars, spindles, and/or shafts may be disposed within a cannula during insertion at a selected insertion site. Inner penetrators may include such trocars, spindles, and shafts, among others. Further, inner penetrators may comprise various lengths including, but not limited to, 20 to 50 millimeters (e.g., between 35 and 40 mm, 38.5 mm, and/or the like). Outer penetrators may include catheters, cannulas, hollow needles, and hollow drill bits, among others. In some implementations, the penetrator assembly may include a flexible outer penetrator and a rigid inner penetrator as disclosed in international patent application no. PCT/IB2019/053900, which is herein incorporated by reference in its entirety.

Figure 3:
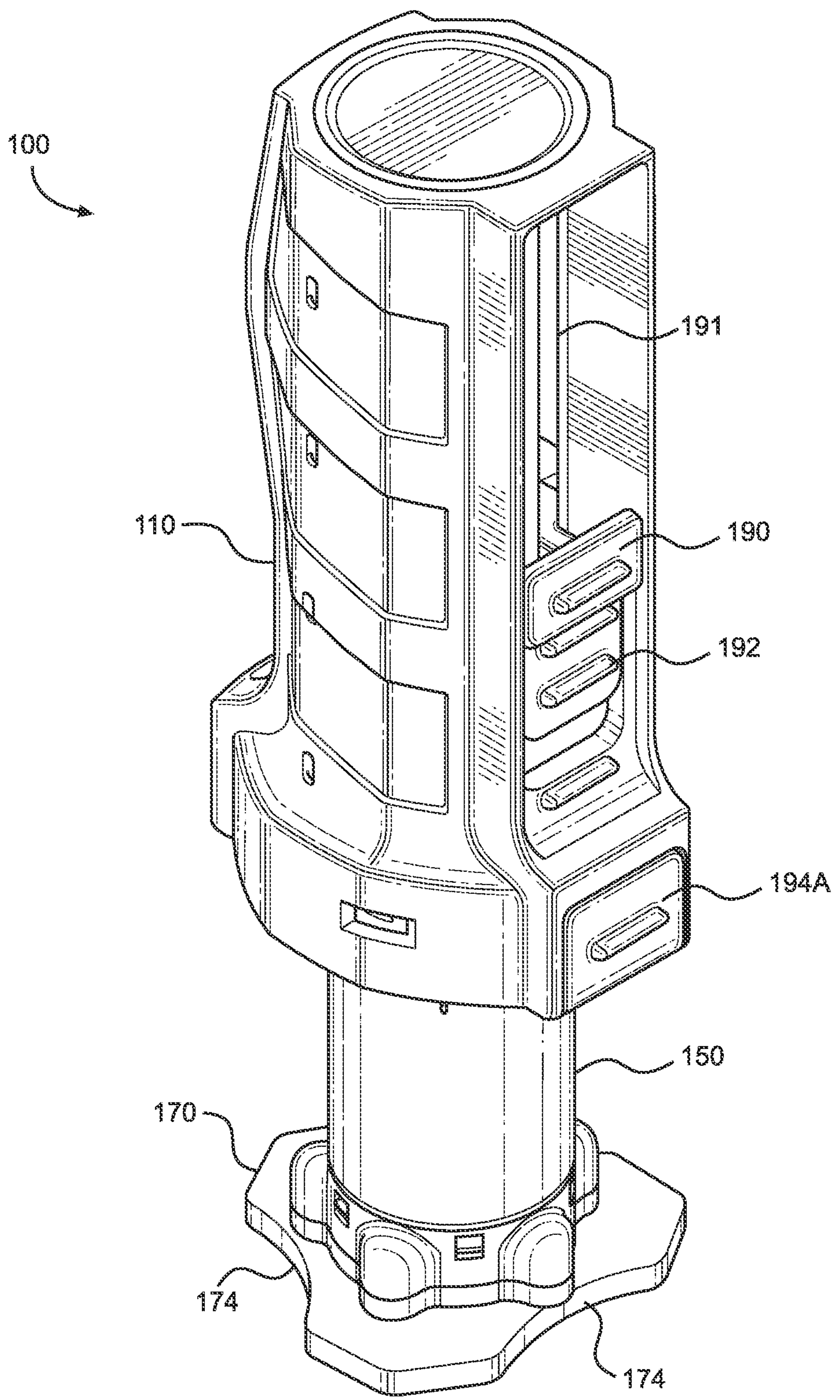
FIG. 3 illustrates a perspective view of an implementation of an intraosseous access device according to the present disclosure.
Figure 4:
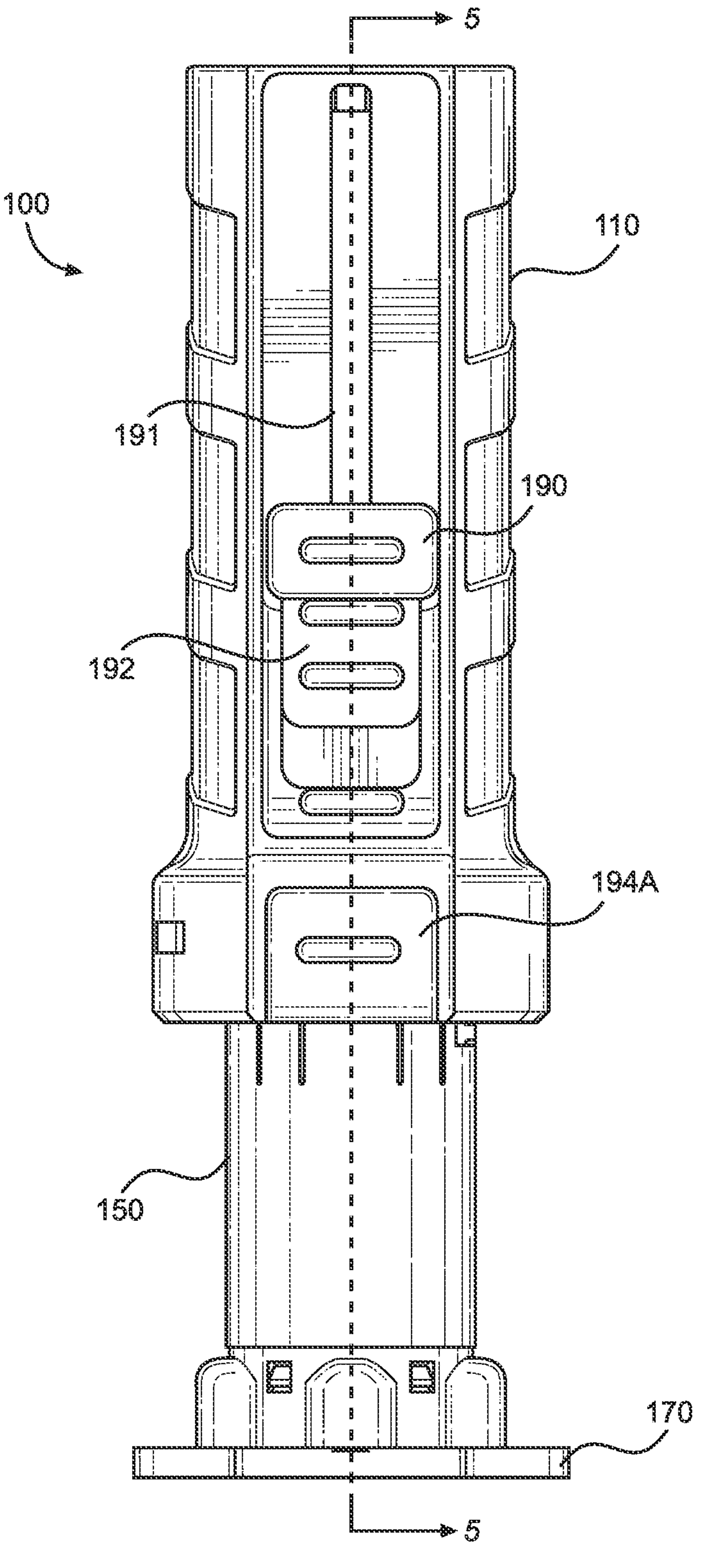
FIG. 4 illustrates a front view of the intraosseous access device of FIG. 3.

FIGS. 3 and 4 depict an implementation of an intraosseous (10) access device 100 and its components. In a first mode of operation, the intraosseous access device is operable to help locate a suitable insertion site and manually penetrate underlying bone, such as a patient's sternum, to quickly and easily provide a conduit to an intraosseous space within the bone for associated medical procedures, including delivery of fluid and medication, aspiration, and biopsy of bone marrow, among others. In a second mode of operation, the intraosseous access device is operable for manual insertion into a patient's intraosseous space at a peripheral insertion site, such as a patient's humerus or tibia among others.

Figure 5:
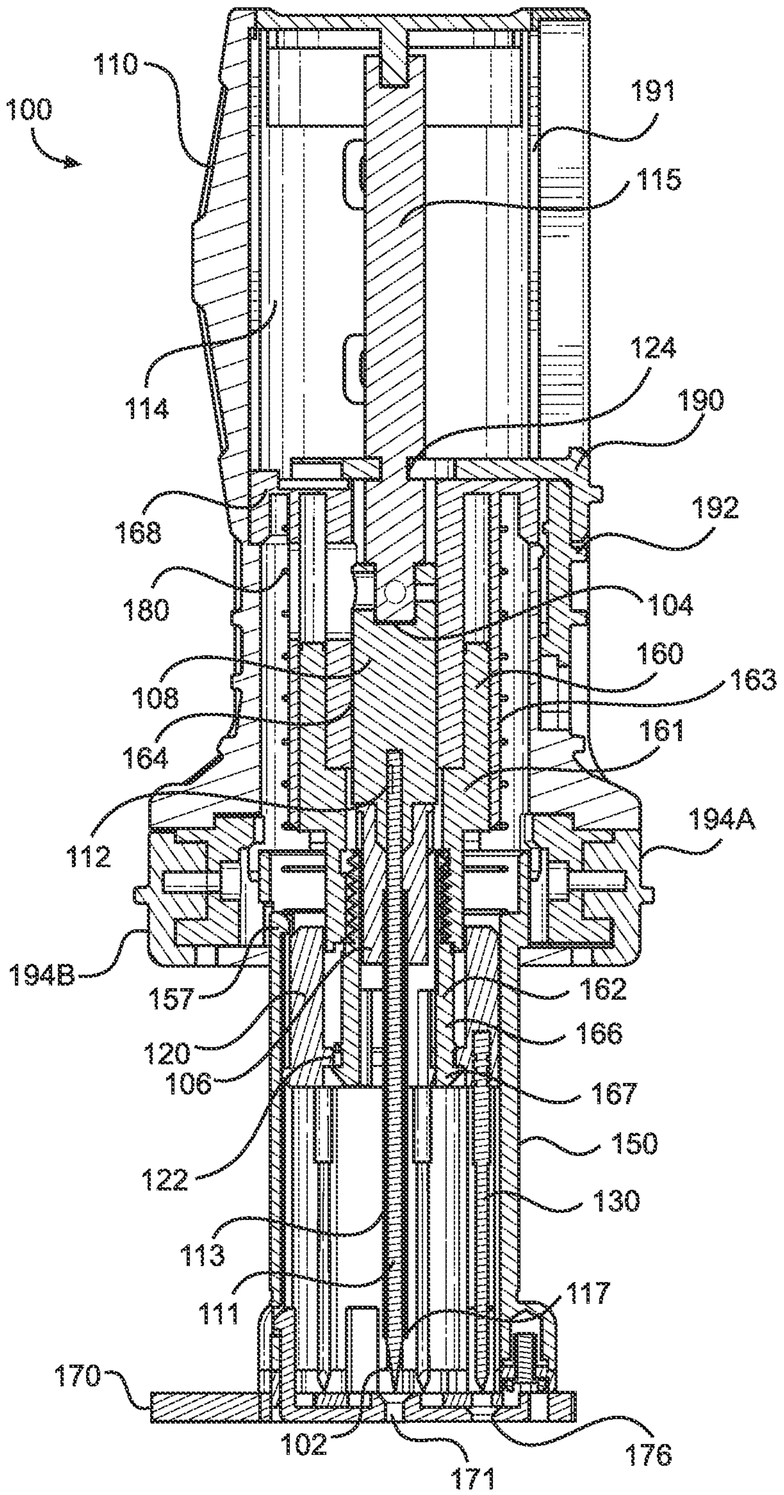
FIG. 5 illustrates a cross-sectional view of the intraosseous access device taken along line 5-5 in FIG. 4.

FIG. 5 depicts the intraosseous access device 100 of the present disclosure in an initial position, or resting state, prior to use in either the first or second modes of operation. The intraosseous access device 100 comprises a housing 105, a bone probe ring 120, a bone probe 130, a telescoping protective shield 150, a retainer 160, a stabilizer base 170, and a biasing member 180, as will be discussed in greater detail below. The intraosseous access device 100 also comprises an inner penetrator hub 108, which is attached to an inner penetrator 111. The inner penetrator 111 may, for example, take the form of any suitable stylet or trocar, as previously discussed above. The inner penetrator 111 includes a distal end having a tip 102 operable to penetrate bone and associated bone marrow. The inner penetrator 111 further includes a proximal end that may have a notch 112 configured to assist in coupling the inner penetrator hub 108 to the inner penetrator 111. For instance, the inner penetrator hub 108 may be over-molded over the proximal end of the inner penetrator 111 such that the material from the inner penetrator hub may be molded to extend into the notch 112. The inner penetrator 111 extends from the distal end 116 of the inner penetrator hub 108.

The manual intraosseous driver assembly 100 also includes an outer penetrator hub 106 that is coupled to an outer penetrator 113. The distal end 116 of the inner penetrator hub 108 is configured to releasably engage a proximal end of the outer penetrator hub 106, as will be discussed in further detail below. The outer penetrator 113 may, for example, take the form of a hollow tube, such as cannula (e.g., a metal cannula), or a hollow drill bit, and which may be configured (e.g., to possess sufficient rigidity) such that the outer penetrator 113 will not buckle or otherwise be damaged as it is inserted through anterior compact bone together with the inner penetrator 111. In other implementations, the outer penetrator 113 may be flexible so that it may be manipulated after insertion into the intraosseous space (i.e., by bending a portion of the outer penetrator to secure it, along with the outer penetrator hub 106, against the patient's skin to provide a low profile). The outer penetrator hub 106 includes a proximal end 107 and a distal end 109. The outer penetrator 113 also includes a proximal end 118 and a distal end 117, the proximal end 118 being coupled to the outer penetrator hub 106. The outer penetrator distal end 117 includes a cutting surface operable to penetrate bone and associated marrow. The outer penetrator 113 extends from the distal end 109 of the outer penetrator hub 106.

The inner penetrator hub 108 is configured to removably attach to the outer penetrator hub 106. More particularly, the proximal end 107 of the outer penetrator hub 106 and the distal end 116 of the inner penetrator hub 108 may be configured as complimentary connectors (with, for example, the distal end 116 of the inner penetrator hub 108 being configured as a male Luer connector and the proximal end 107 of the outer penetrator hub 106 being configured as a female Luer connector, although these configurations could be reversed in other implementations such that the distal end 116 of the inner penetrator hub 108 is configured as a female Luer connector and the proximal end 107 of the outer penetrator hub 106 is configured as a male Luer connector). Further, a distal end 116 of the inner penetrator hub 108 may include a male projection that is tapered to match an inwardly-tapered passageway at the proximal end 107 of the outer penetrator hub 106.

The outer penetrator 113 comprises a longitudinal passageway configured to slidably receive a portion of the inner penetrator 111 when the inner penetrator hub 108 is attached to the outer penetrator hub 106, thus forming a penetrator assembly. The intraosseous access device 100 is configured to manually drive the penetrator assembly into an intraosseous space. In particular, the intraosseous access device 100 comprises a housing 105 having an outer sleeve 110 defining a handle. The handle has a shape suitable for grasping during manual insertion of the inner and outer penetrators into the bone and associated bone marrow. The handle is further configured to allow manual force to be applied to the penetrator assembly and at the same time permit rotation of the handle during insertion of the penetrator assembly into the intraosseous space. The handle may also include a textured outer surface to provide an anti-slip grip for the user. The handle may also be ergonomically contoured to provide a comfortable grip for the user.

When the inner penetrator hub 108 and the outer penetrator hub 106 are coupled to each other, the inner penetrator 111 is disposed within the passageway of the outer penetrator 113, and the inner penetrator tip 102 extends beyond the distal end 117 of the outer penetrator 113. The inner penetrator tip 102 and the outer penetrator distal end 117 are each operable to penetrate bone and associated bone marrow. More particularly, the inner penetrator tip 102 and the outer penetrator distal end 117 are configured to cooperate with each other to form a penetrator assembly tip operable to penetrate bone and associated bone marrow when the inner penetrator hub 108 is attached to the outer penetrator hub 106.

The tip 102 of the inner penetrator 111 is pointed and configured to allow the intraosseous access device 100 to be driven into an intraosseous space, such as intraosseous space 16. The inner penetrator 111 fits closely within the passageway of the outer penetrator 113 such that the inner penetrator 111 prevents the outer penetrator 113 from becoming clogged with tissue (e.g., skin, bone, marrow) as the intraosseous access device is driven into an insertion site of a subject (e.g., a patient). The inner penetrator tip 102 and the outer penetrator distal end 117 may be ground together to form corresponding cutting surfaces in some implementations where both the inner penetrator 111 and the outer penetrator 113 comprise a suitable metal. In other implementations, the inner penetrator tip 102 and the outer penetrator distal end 117 may be ground separately to form corresponding cutting surfaces configured to penetrate bone and associated marrow, and where the corresponding cutting surfaces of the inner and outer penetrators cooperate with each other to penetrate the bone and associated marrow. Once the intraosseous access device is properly positioned at a target insertion site and intraosseous access is achieved by the penetrator assembly, the inner penetrator hub 108 can be disengaged from the outer penetrator hub 106 such that the proximal end 107 (which may take the form of a male or female Luer lock) of the outer penetrator hub is exposed and a conduit is formed from the outer penetrator hub 106 through the outer penetrator 113 to the intraosseous space. A fluid source may then be coupled to the proximal end 107 of the outer penetrator hub 106 to deliver fluid through the outer penetrator 113 into the intraosseous space.

The housing 105 defines an internal cavity 114. The housing 105 also includes a housing core 115, such as a rod or column, disposed within the cavity 114. A proximal end 119 of the inner penetrator hub 108 includes a recess 104 configured to receive a distal portion of the housing core 115. A proximal portion of the housing core 115 is coupled to a proximal end the housing 105. In some implementations, the housing core 115 may be integrally formed with the proximal end of the housing. The housing core 115 includes a thin neck region 124 configured to engage an actuator, such as a slider 190, operable to lock the retainer 160 in a first, or deployed, position relative to the outer sleeve when the intraosseous access device 100 is in a first mode of operation for locating a suitable insertion site and manually penetrating underlying bone, such as a patient's sternum, to quickly and easily provide a conduit to an intraosseous space within the bone. A slide lock 192 is slidingly attached to a longitudinal track or side channel 191 formed on the outer sleeve 110. The slide lock 192 abuts a tab portion of the slider 190 when in a locked position. The slide lock 192 is operable to slide out of abutment with the tab portion of the slider when in an unlocked position. The slider 190 is operable to disengage the thin neck portion 124 of the housing core 115 to allow the retainer 160 to move to a second, or undeployed, position relative to the outer sleeve 110 when the intraosseous access device is in a second mode of operation for manual insertion of the penetrator assembly into a patient's intraosseous space at a peripheral insertion site.

The outer sleeve 110, the bone probe ring 120, and the protective shield 150 each have a generally cylindrical or tubular shape. An exterior surface of the outer sleeve 110 includes a longitudinal track 191 configured to guide the slider 190 from a first position in which the intraosseous access device is in the first mode of operation for sternal intraosseous access, to a second position in which the intraosseous access device is in the second mode of operation for peripheral intraosseous access. The bone probe ring 120 includes a distal end 123 having an outwardly protruding annular flange 122. The bone probe ring 120 further includes a passageway configured to slidably receive a distal portion of the retainer 160.

The distal end of the bone probe ring 120 further includes a plurality of circumferentially spaced apart openings from which respective bone probes 130 extend. For instance, the distal end of the bone probe ring may include five openings corresponding to five bone probes, although other implementations may have more or less openings and corresponding bone probes. In some implementations, a single bone probe may be provided. In other implementations, a plurality of bone probes (for example, two or more bone probes, and preferably three bone probes) may be provided. The bone probes may be arranged so that they stabilize the intraosseous access device during insertion of a penetrator assembly into the intraosseous space at a desired location and orientation. For example, three bone probes may be arranged in a triangle surrounding the inner and outer penetrators.

Figure 6A:
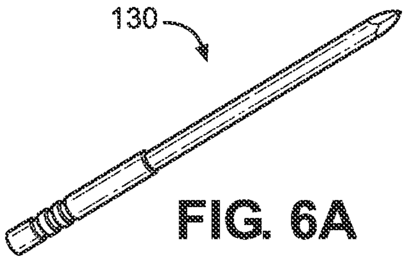
FIG. 6A illustrates a perspective view of an implementation of a bone probe in accordance with the present disclosure.
Figure 6B:
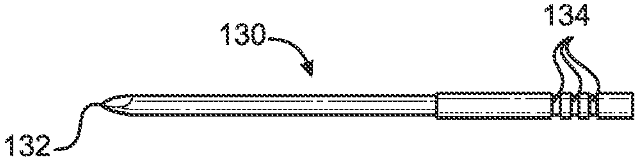
FIG. 6B illustrates a side elevational view of the bone probe of FIG. 6A.
Figure 6C:
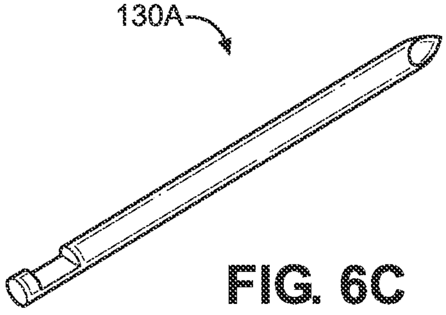
FIG. 6C illustrates a perspective view of another implementation of a bone probe in accordance with the present disclosure.
Figure 6D:
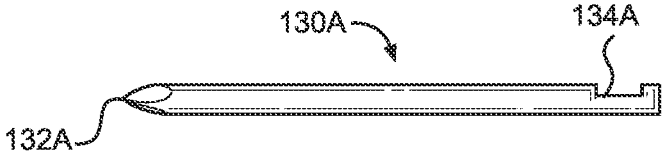
FIG. 6D illustrates a side elevational view of the bone probe of FIG. 6C.

As shown in FIGS. 6A and 6B, each probe 130 comprises a pointed tip 132, a plurality of circumferential grooves or notches 134, and a proximal end 136, where the annular notches 134 are closer to the proximal end 136 than to the tip 132. The probes 130 may comprise stainless steel, though other suitable sterile or biocompatible materials (or materials capable of being made sterile before use on a patient) may be used. The proximal end 136 is configured to be inserted into the respective opening in the distal end 123 of the bone probe ring 120. In some implementations, the bone probes 130 may be fixed to the bone probe ring 120, such as by being bonded using UV-curable adhesive applied to the annular grooves 134 and/or the proximal end 136 of the probe 130. In other implementations, the bone probes 130 may be force fit through the respective openings such that they are held in place by an interference fit. In still other implementations, the probes 130 may be fixed to the bone probe ring 120 as part of an injection molding process or using epoxy. FIGS. 6C and 6D depict another implementation of bone probes 130*a* that are suitable for use with the intraosseous access device 100. Each probe 130*a* comprises a pointed tip 132*a*, a groove or notch 134*a*, and a proximal end 136*a*, where the notch 134*a* is closer to the proximal end 136*a* than to the tip 132*a*. Each probe 130*a* may comprise stainless steel, though other suitable sterile or biocompatible materials (or materials capable of being made sterile before use on a patient) may be used. The proximal end 136*a* is configured to be inserted into the respective opening in the distal end 123 of the bone probe ring 120. Probes 130*a* may be fixed to the bone probe ring 120, such as by being bonded using UV-curable adhesive applied to the notch 134*a* and/or the proximal end 136*a* of the probe 130*a*. In other implementations, the probe 130*a* may be force fit in the respective opening in the flange of the bone probe ring 120, thus being held in place by an interference fit. In other implementations, the probes 130*a* may be fixed to the bone probe ring 120 as part of an injection molding process or using epoxy. Each probe 130, 130*a* may comprise any of various lengths.

The bone probe ring 120 is slidably disposed within the protective shield 150. The internal cavity 114 is configured to slidably receive the protective shield 150. The retainer 160 includes a first retainer segment 161 threadedly engaged to a second retainer segment 162. A third retainer segment 163 is coupled to the second retainer segment 162. The three retainer segments coupled together form a three-piece chassis. A distal end of the second retainer segment 162 is slidably coupled to the bone probe ring 120 and is configured to allow the bone probe ring to slidably move between a first or extended position and a second or retracted position. The retainer 160 has an internal passageway 164 configured to receive the inner and outer penetrator hubs 108, 106. The proximal end of the third retainer segment 163 includes an outwardly protruding annular flange 168. The distal end of the second retainer segment 162 includes a plurality of resilient fingers 166 annularly disposed along a circumference of the second retainer segment, each finger including a respective ridge or nub 167 protruding radially outward therefrom.

The protective shield 150 includes a proximal end having an annular inner shoulder 157. The biasing member is disposed between the protective shield shoulder 157 and the retainer flange 168, as will be discussed in greater detail below. The protective shield 150 is operable to move between a first or extended position to provide sharps protection from the distal ends of the inner and outer penetrators 111, 113 as well as the bone probes 130, and a second or retracted position to expose the respective inner and outer penetrators 111, 113 and the bone probes 130 during an insertion procedure. The respective ridges or nubs 167 disposed on the resilient fingers 166 of the second retainer segment 162 are configured to engage an inwardly protruding annular flange of the bone probe ring 120 to limit how far the bone probe ring and respective bone probes extend relative to the retainer and the protective shield. The distal end of the bone probe ring may comprise a radially outward protruding annular flange configured to engage the annular shoulder 157 of the protective shield 150 to limit how far the protective shield may extend from the outer sleeve 110 when the shield is in the first or extended position. When the protective shield 150 is in the first or extended position, the tips 132 of each bone probe 130 are disposed within the interior space of the protective shield to provide sharps protection. When the protective shield is in a second or retracted position, the tips 132 of each bone probe 130 extend from the distal end of the shield.

A stabilizer base 170 is connected to the telescoping shield 150. The base 170 comprises a guide hole 171 configured to guide the penetrator assembly during an insertion procedure. The base 170 also comprises a plurality of through-holes 176 corresponding to, and aligned with, the bone probes 130. The through-holes 176 are configured to permit passage of the respective bone probes 130 through the base 170 during an insertion procedure. The base 170 may also comprise an alignment feature 174, such as an arc-shaped cutout portion of the base. The alignment cutout 174 is configured to approximate the shape of the sternal notch of a human patient and is operable to indicate proper placement of the base 170 against the patient. The intraosseous access device 100 is properly located on the chest of a patient when the base 170 is placed over the sternum, for instance during the first mode of operation, such that the sternal notch is visible and at least partially (and, preferably, completely) bounded by the alignment cutout 174.

Figure 15:
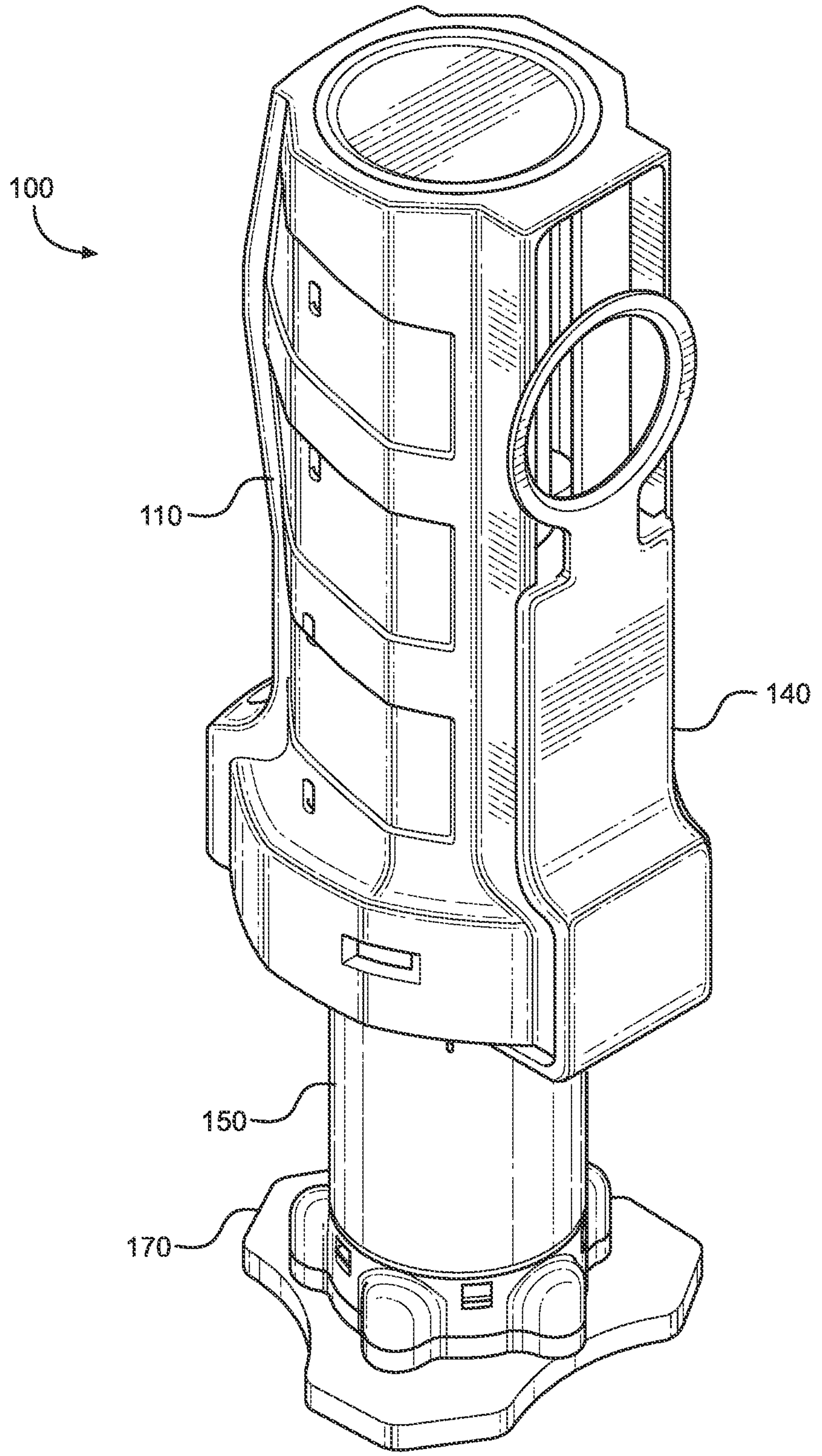
FIG. 15 illustrates a perspective view of an intraosseous access device of FIG. 3 with a safety latch.
Figure 16:
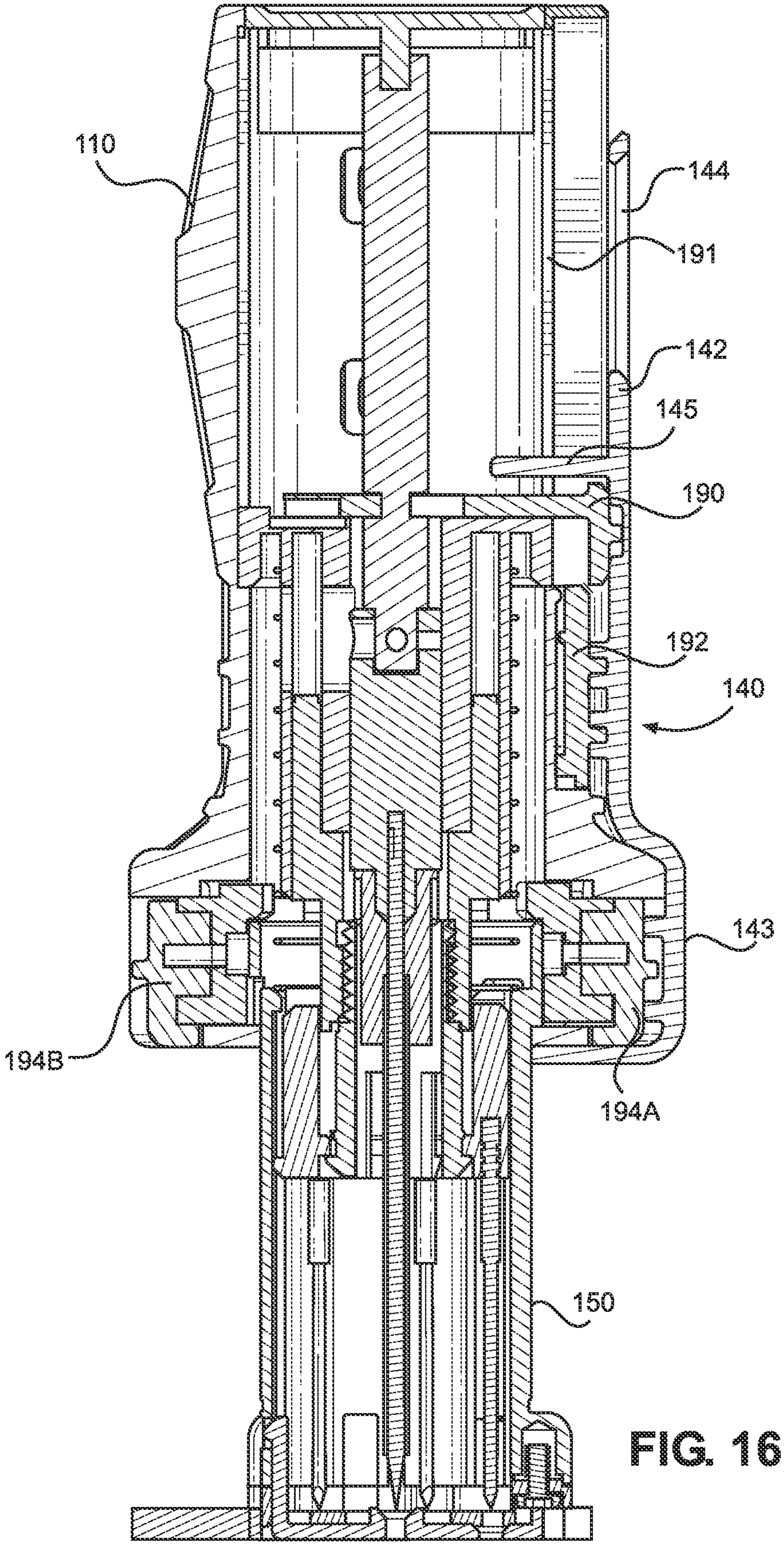
FIG. 16 illustrates a cross-sectional side elevation view of the intraosseous device with the safety latch of FIG. 15.

Referring briefly to FIGS. 15 and 16, the intraosseous access device 100 may further include a removable safety latch 140 operable to prevent the protective shield 150 from moving from the first or extended position to the second or retracted position. In particular, the safety latch 140 includes a first end 142 configured to engage the outer sleeve 110. Further, the safety latch 140 includes a second end 143 configured to prevent the protective shield 150 from moving to its second or retracted position. The first end 142 of the latch 140 includes a pin portion 145 configured to be inserted within the longitudinal track 191 to engage the side channel in the outer sleeve to block the slider 190 from sliding from a first position to a second position. The second end 143 of the latch 140 is configured to depress a safety button 194A to prevent the shield 150 from telescopically retracting into the outer sleeve 110 toward its second or retracted position in order to maintain sharps protection of the penetrator assembly and the bone probes. A user may remove the safety latch 140 from the intraosseous access device 100 by pulling a tab 144 to disengage the pin 145 from the side channel of the outer sleeve 110, thus allowing the slider 190 to be actuated to manually retract the telescoping protective shield. Removal of the safety latch also stops the first safety button 194A from being pressed so as to unlock the protective shield 150 from its extended position.

As previously described, the intraosseous access device 100 may be used in a first mode of operation to help locate a suitable insertion site and manually penetrate underlying bone, such as a patient's sternum, for quickly and easily providing a conduit to an intraosseous space within the bone. Prior to use, in an initial position of the first mode of operation, the protective shield 150 is in its first or extended position, as shown in FIG. 5. In operation, a user first must remove the safety latch 140 from the intraosseous access device by pulling on the tab 144, thereby disengaging the pin 145 at the first end 142 from the side channel of the outer sleeve 110 before the intraosseous access device can be used in an intraosseous insertion procedure. The pin prevents operation of the intraosseous access device when inserted into the channel by blocking the shield 150 from telescopically retracting into the outer sleeve 150. The locking pin may be inserted during manufacture or before use of the intraosseous access device, and removed to prepare the intraosseous access device for use.

Figure 7:
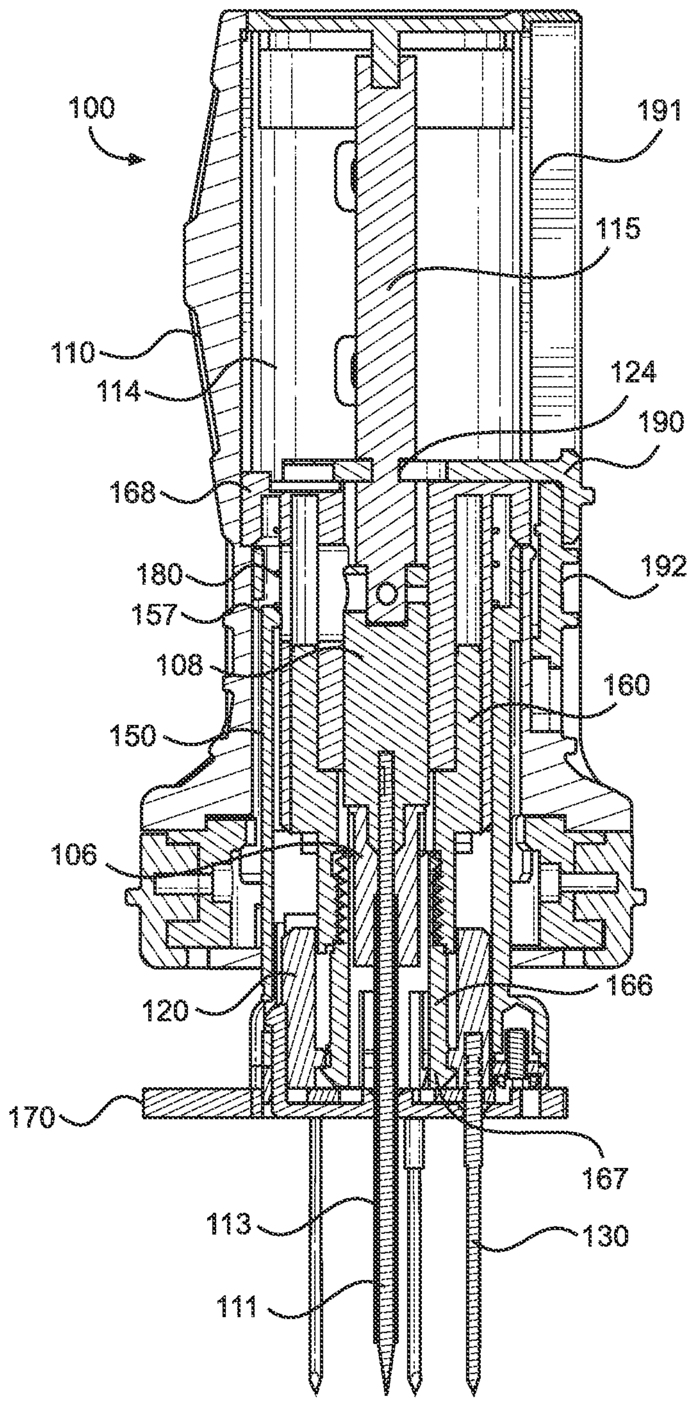
FIG. 7 illustrates a cross-sectional side elevation view of the intraosseous access device of FIG. 5 during use in a first mode of operation.

The intraosseous access device may be operated by placing the stabilizer base 170 against the skin of a patient over a bone, such as the sternum, into which it is desired to insert the penetrator assembly. The stabilizer base 170 has an arc-shaped alignment cutout 174 that helps a user align the intraosseous access device with a patient's sternal notch. In other implementations, one or more guide features may be provided to facilitate alignment with anatomical landmarks at other infusion sites. Once the stabilizer base 170 is aligned with and placed against the insertion site, the user operates the intraosseous access device by first pushing down on the handle 110, as depicted in FIG. 7. As the handle 110 is pushed, the protective shield 150 telescopically retracts into the internal cavity 114 of the outer sleeve to move from its first or extended position to its second or retracted position. The biasing member 180 is disposed between the flange 168 at the proximal end of the third retainer segment 163 and the shoulder 157 at the proximal end of the protective shield 150. The biasing member 180, such as a compression spring, is operable to bias the protective shield toward its extended position. The protective shield is thus urged against the biasing force of the biasing member 180 as it is retracted into the internal cavity of the outer sleeve. As the protective shield 150 telescopically retracts into the outer sleeve 110, the penetrator assembly 111, 113, as well as the surrounding bone probes 130, protrude from the stabilizer base 170 to penetrate the patient's skin and underlying soft tissue. The stabilizer base 170 assists in keeping the intraosseous access device 100 over the desired insertion site and in the desired orientation. During use, the stabilizer base 170 is substantially perpendicular to the penetrator assembly and assists in introducing the inner and outer penetrators 111, 113 straight into the patient's sternum.

Figure 8:
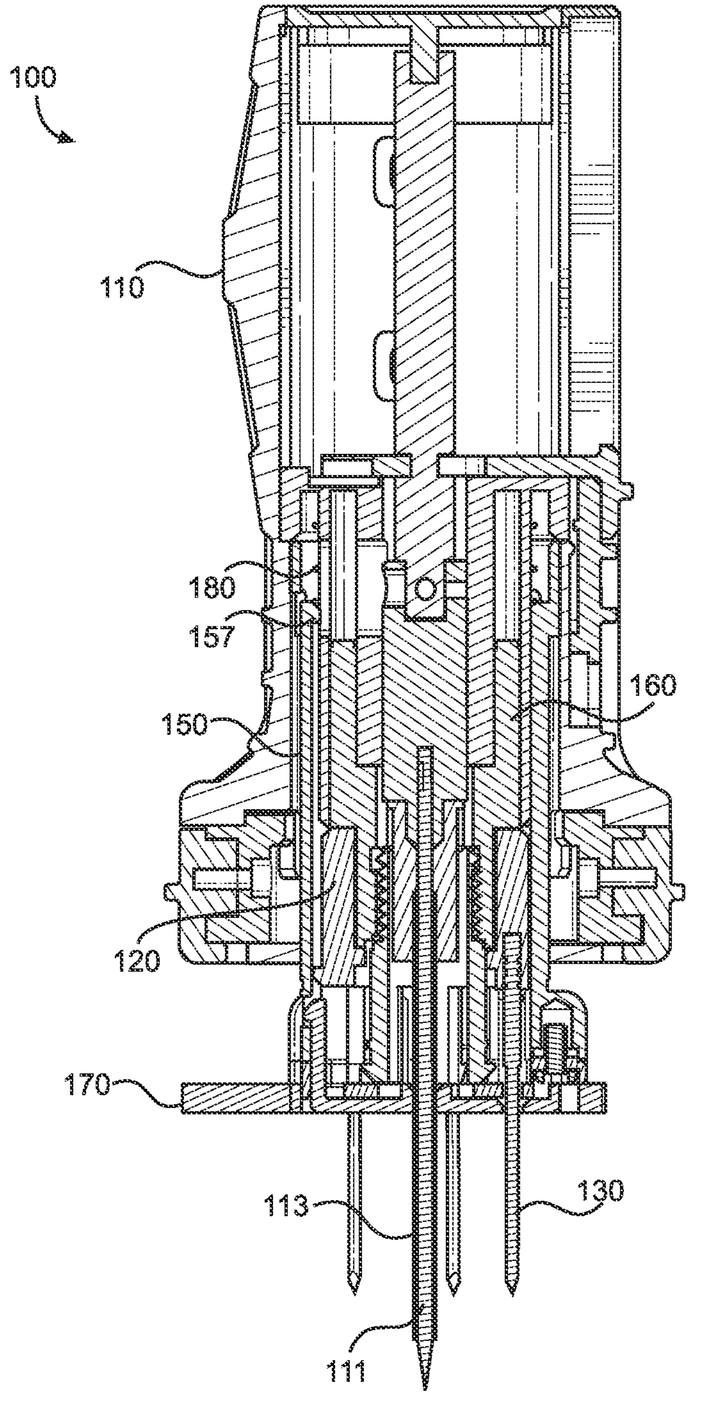
FIG. 8 illustrates a cross-sectional side elevation view of the intraosseous access device of FIG. 5 during use in a first mode of operation.

A first depth of insertion of the inner and outer penetrators 111, 113 is determined when the tips 132 of the respective bone probes 130 contact the bone. At this first depth of insertion, the inner and outer penetrators 111, 113 are inserted the same distance as the bone probes 130, and therefore the inner and outer penetrators do not yet penetrate into the intraosseous space. Insertion of the inner and outer penetrators 111, 113 to a second depth of insertion (e.g., into the intraosseous space) is then carried out by the user pushing the handle 110 again to continue retracting the protective shield 150 into the outer sleeve 110, such that a surface of the base 170 may contact the bone probe ring 120 to correspondingly slide the bone probe ring 120 and the associated bone probes 130 into the cavity 114 of the outer sleeve 110, as shown in FIG. 8. Such retraction of the bone probes and bone probe ring into the outer sleeve is moreover a result of further penetration of the penetrator assembly into the intraosseous space while the force applied by the bone probes to the anterior cortex of the bone causes the bone probe ring to slide upward to its retracted position. In other words, the protective shield 150 is moved from its first or extended position to its second or retracted position to deploy the inner and outer penetrators 111, 113 into the intraosseous space. Moreover, the retainer 160 and the outer sleeve 110 are rotatable relative to the bone probe ring 120. Thus, the user may also rotate the handle while pushing it in order to facilitate penetration of the penetrator assembly into the bone without disturbing the position of the bone probe ring or the placement of the bone probes.

As the bone probe ring 120 slides into the internal cavity of the outer sleeve 110, an internal annular flange 125 of the bone probe ring 120 no longer abuts the corresponding ridges or nubs 167 protruding outwardly from the second retainer segment 162. The bone probe ring 120 is operable to be retracted into the cavity of the outer sleeve until a proximal end of the bone probe ring abuts an annular overhang portion of the first retainer segment 161, or until the internal annular flange 125 of the bone probe ring abuts a shoulder portion of the second retainer segment 162. Further, the bone probe ring 120 may not be spring loaded. Rather, the bone probe ring may be held in its distal position via detents on the chassis, or more particular, via a pair of detents on the distal end of the second retainer segment 162. Once the bone probes are set against the anterior cortex of the patient's sternum, the internal annular flange 125 of the bone probe ring is operable to overcome a first detent to allow the bone probe ring to float until the penetrator assembly is advanced a set distance (i.e., approximately 10 millimeters) beyond the bone probe tips and into the intraosseous space. Once the bone probe ring is moved back by the set distance, the internal annular flange 125 snaps into a second set of detents to secure the bone probe. An audible and/or tactile feedback may be provided to the user as the flange 125 snaps into the second set of detents. Such feedback indicates to the user deployment of the penetrator assembly into the intraosseous space.

Thus, the bone probe ring is configured to move between a first position and a second position during the first mode of operation, where the bone probe ring is closer to the distal retainer end of the retainer when the bone probe ring is in the first position than when the bone probe ring is in the second position. The distal end of the bone probe ring includes an inwardly protruding nub configured to engage a first detent on the retainer to maintain the bone probe ring in the first position during the first mode of operation. The nub is configured to engage a second detent on the retainer to maintain the bone probe ring in the second position during the first mode of operation. The nub is operable to snap into the second detent on the retainer, and a feedback is provided to a user when the nub is snapped into the second detent on the retainer. The feedback may comprise at least one of an audible response and a tactile response to indicate insertion of the penetrator assembly into the intraosseous space.

Figure 9:
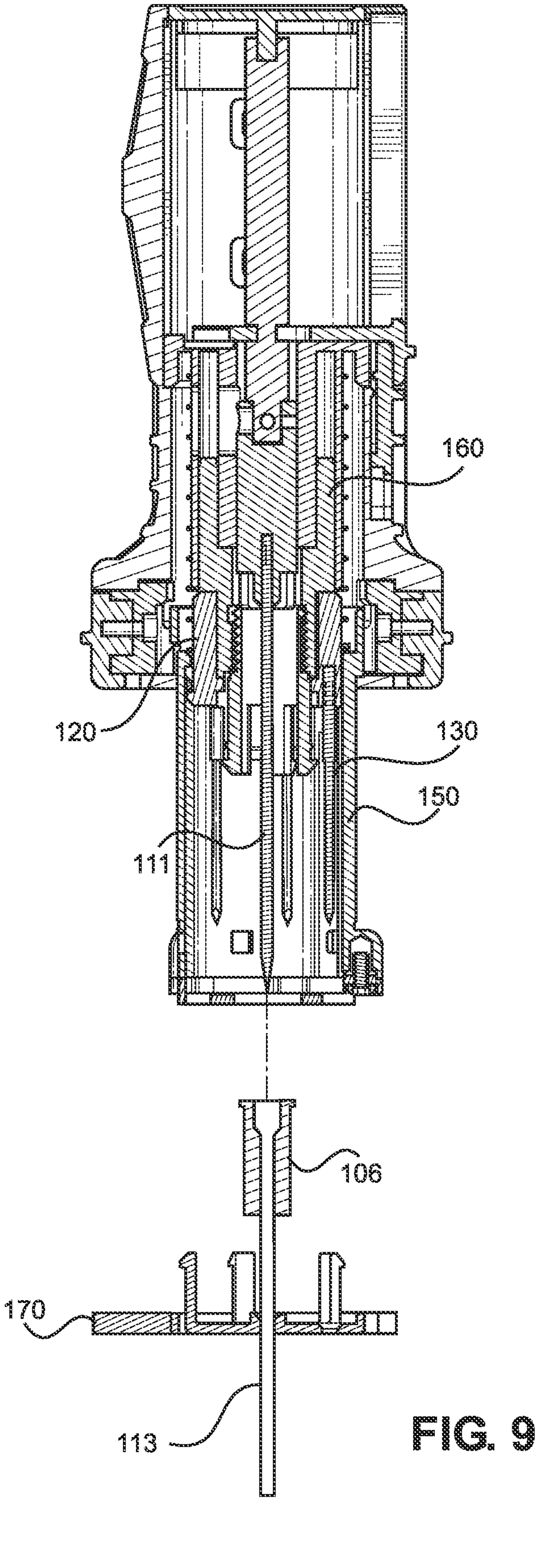
FIG. 9 illustrates a cross-sectional side elevation view of the intraosseous device of FIG. 5 during use in a first mode of operation.

As shown in FIG. 9, once the inner and outer penetrators 111, 113 have penetrated the patient's bone to a desired depth, a release mechanism uncouples the stabilizer base 170 from the protective shield 150. The release mechanism may include one or more flexible latches on the stabilizer base each configured to releasably engage a respective catch at the distal end of the protective shield. The outer penetrator hub 106 is also uncoupled from the inner penetrator hub 108 (and thus the outer penetrator 113 is likewise uncoupled from the inner penetrator 111). The depth of penetration is preferably set so that insertion of the inner and outer penetrators 111, 113 will stop once their respective tips enter the intraosseous space and are in the patient's bone marrow. After the release mechanism is triggered, the remainder of the intraosseous access device 100 may be withdrawn from the insertion site to leave in place the stabilizer base 170, the outer penetrator hub 106, and the outer penetrator 113 at the insertion site.

Figure 10:
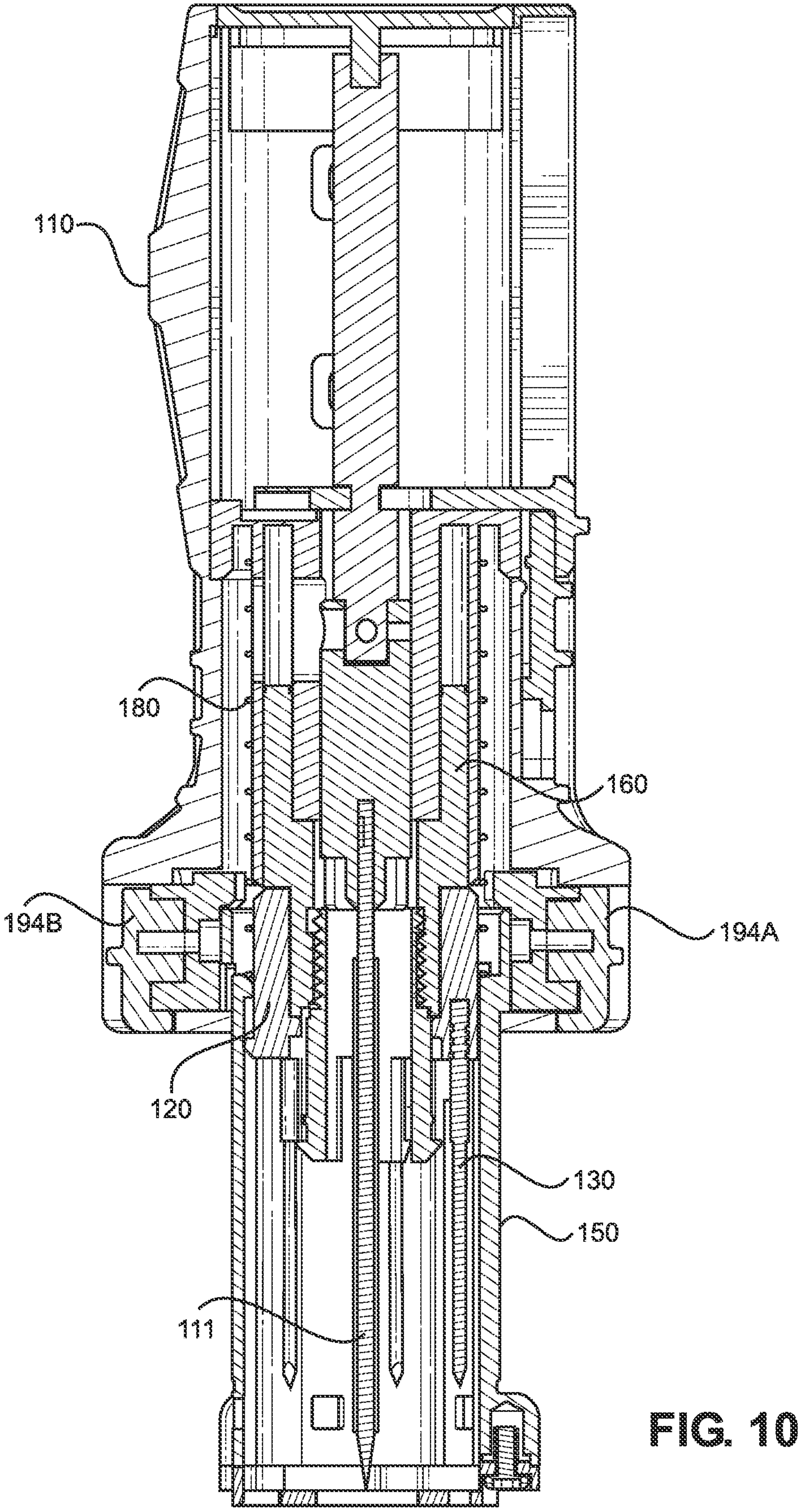
FIG. 10 illustrates a cross-sectional side elevation view of the intraosseous access device of FIG. 5 during use in a first mode of operation.

As the rest of the intraosseous access device is removed from the insertion site, as shown in FIG. 10, the biasing member 180 is operable to return the protective shield 150 back to its extended position from its retracted position. In particular, the biasing member 180, such as a compression spring, is disposed between the flange 168 on the third retainer segment 163 and a shoulder 157 on the proximal end of the protective shield. The biasing member 180 urges the protective shield back to its first or extended position in order to provide sharps protection for the inner penetrator tip 102 as well as the bone probe tips upon their removal from the insertion site.

Thus, removal of the intraosseous access device from the insertion site automatically moves the telescoping protective shield 150 from its second or retracted position within the internal cavity of the outer sleeve back to its first or extended position so as to protect any users from inadvertent contact with the bone probes 130 and the sharp inner penetrator tip. After the protective shield 150 is urged back to its extended position, the user may depress one or both of the safety buttons 194A, 194B that are operable to lock the protective shield in the extended position. Each of the safety buttons 194A, 194B has an overhang portion configured to abut the interior shoulder 157 of the protective shield 150 when in the extended position in order to block the shield from telescopically retracting back into the internal cavity of the outer sleeve.

In some implementations, the stabilizer base 170 may be adhered to the patient's skin to protect the infusion site and to provide an anchor for strain relief for any tubing that may be coupled to the infusion tube assembly, or to provide strain relief for other tubing systems, catheters, or the like. Further, a flexible outer penetrator may be utilized so that it may be manipulated and fixed to the patient after the stabilizer assembly is removed in order to provide a lower profile (i.e., by bending the outer penetrator down to secure it against the skin).

Figure 11:
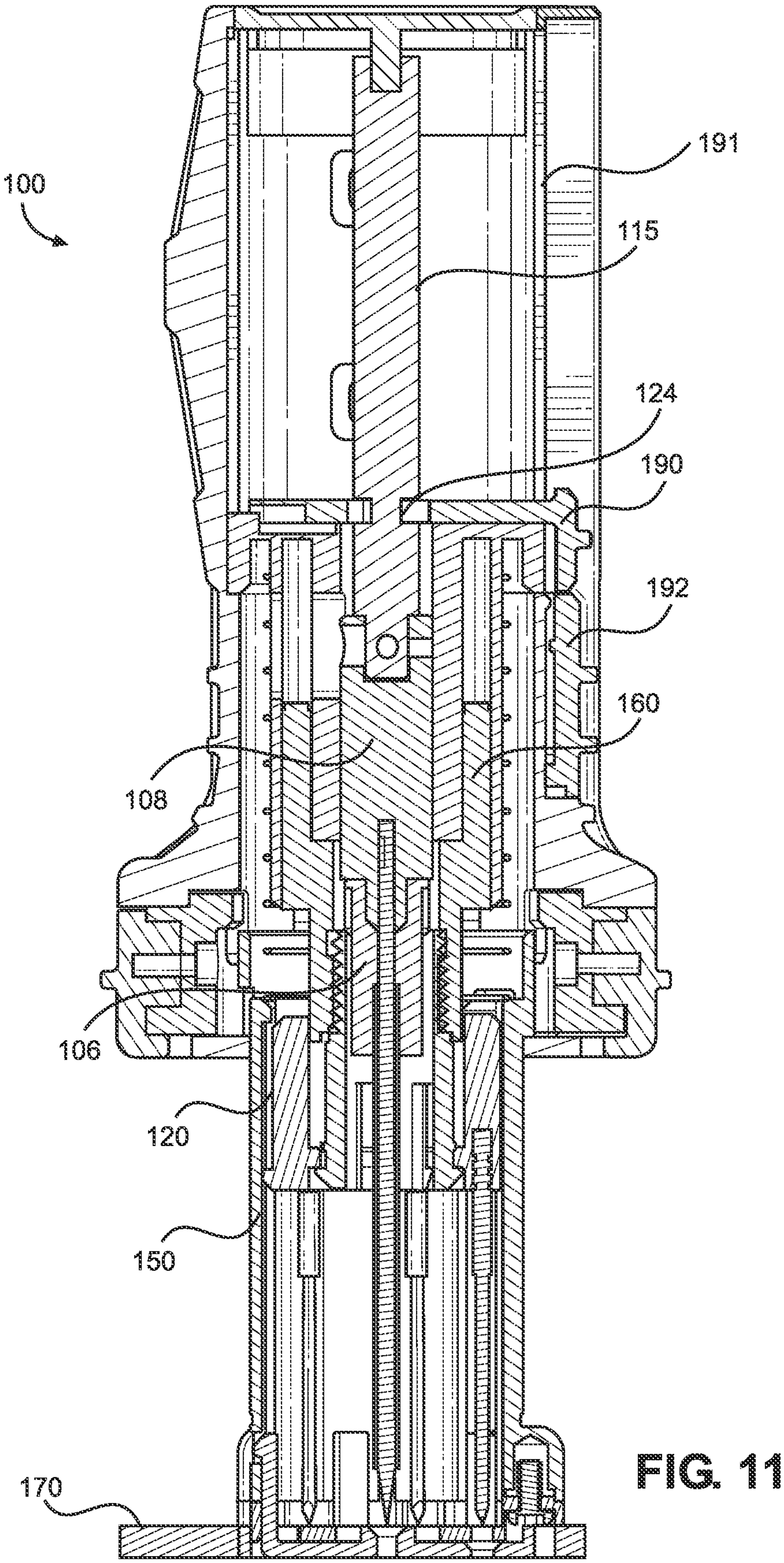
FIG. 11 illustrates a cross-sectional side elevation view of the intraosseous device of FIG. 5 during use in a second mode of operation.

In a second mode of operation, the intraosseous access device 100 is operable for manual insertion into a patient's intraosseous space at a peripheral insertion site. Prior to use, in an initial position of the second mode of operation, both the outer sleeve 110 and the protective shield 150 are in their respective first or extended positions, as shown in FIG. 11. In this second mode of operation, the user is able to manually retract the protective shield 150 prior to intraosseous insertion so that the penetrator assembly can be manually driven into an intraosseous space at a peripheral insertion site.

Figure 12:
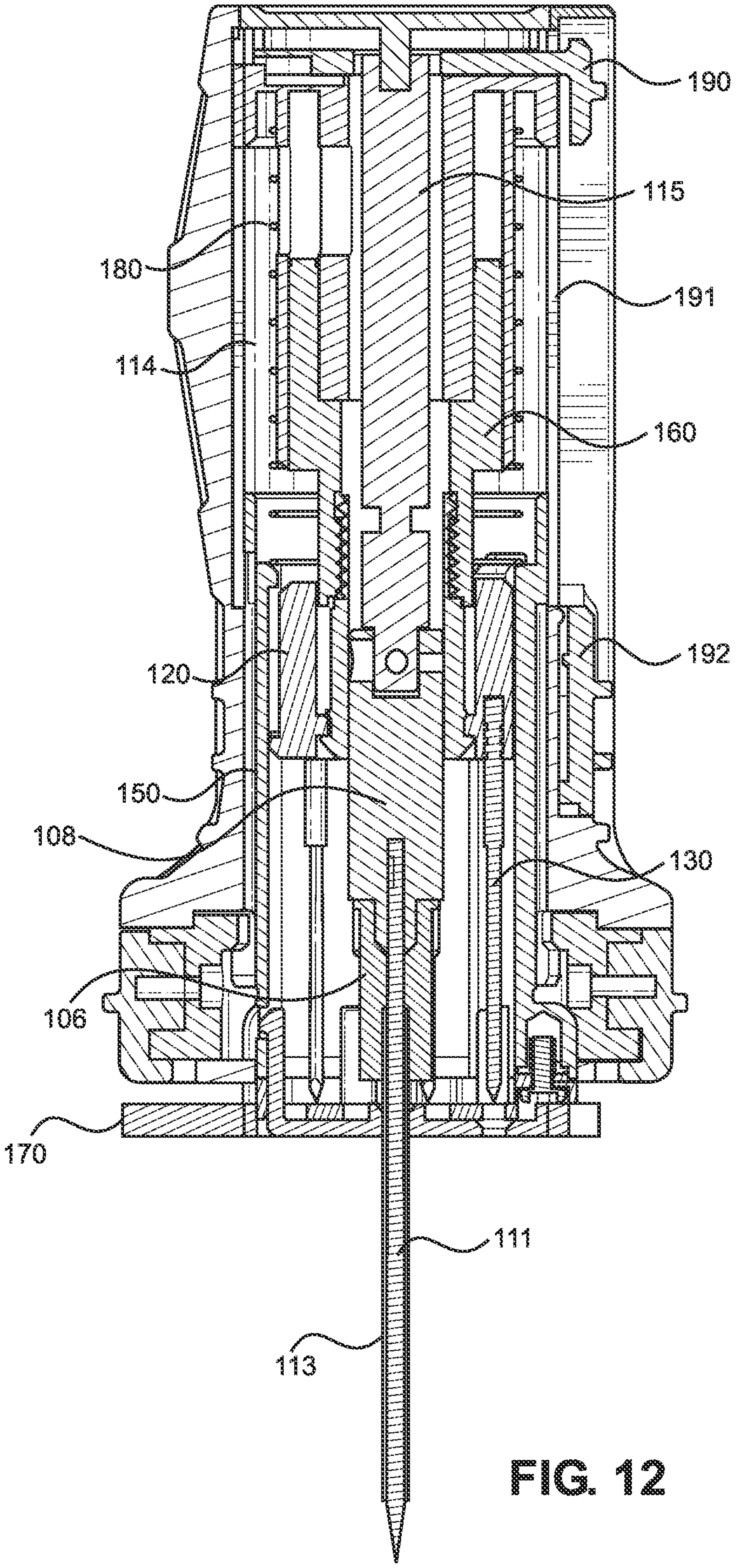
FIG. 12 illustrates a cross-sectional side elevation view of the intraosseous device of FIG. 5 during use in a second mode of operation.

In the second mode of operation, the user first must remove the safety latch 140 in the same manner as described above with regard to the first mode of operation. Next, the user slides the slide lock 192 out of engagement with a tab portion of the slider 190 so that the slider can be depressed. Pressing the slider 190 aligns a slider aperture with the neck 124 of the housing core 115 such that the user can manually slide the retainer 160, the bone probe ring 120 with bone probes, and the protective shield 150 to a retracted position into the internal cavity 114 of the outer sleeve 110, as shown in FIG. 12. Consequently, the inner and outer penetrators 111, 113 protrude from the retracted stabilizer base 170 so that the user can manually insert the penetrator assembly into an intraosseous space by applying force and twisting or rotating the handle 110 back and forth. Accordingly, the retainer 160, the bone probe ring 120 with bone probes 103, and the protective shield 150 are manually retracted upward relative to and inside the handle without applying any force to the biasing member 180 (i.e., without compressing the compression spring). Thus, in the second mode of operation, the manual intraosseous access device 100 may be used for insertion of the inner and outer penetrators 111, 113 into an intraosseous space at a peripheral insertion site by manually pushing and twisting the handle.

Figure 13:
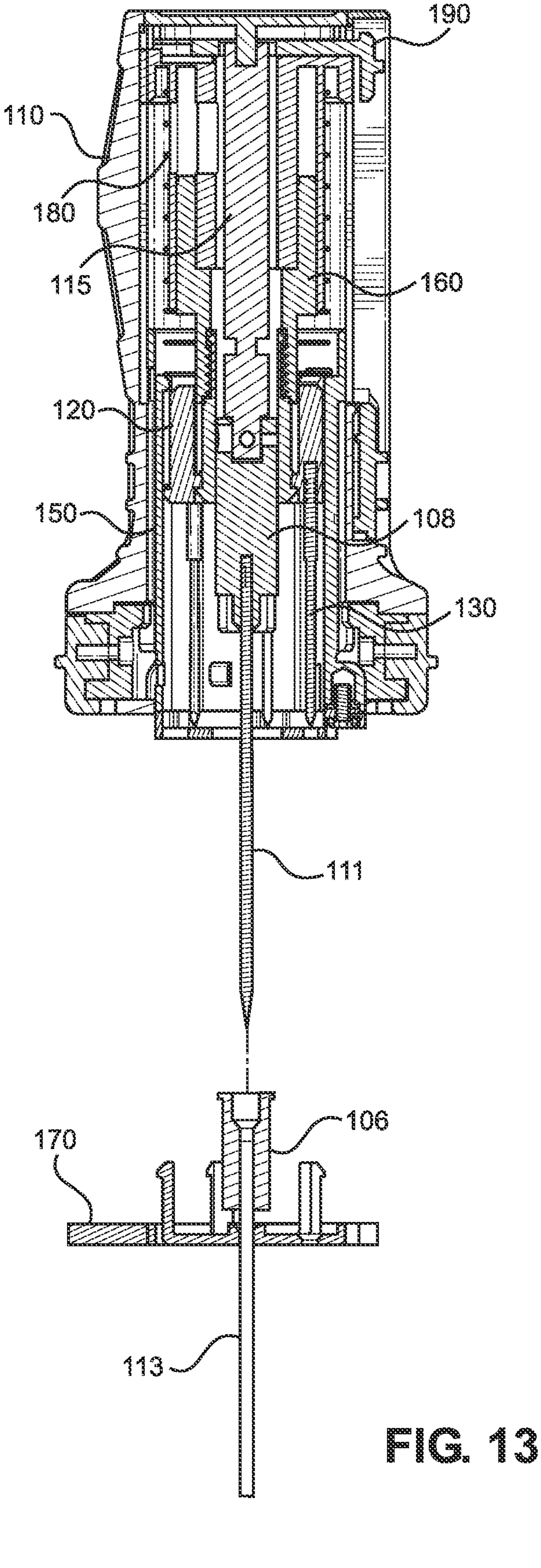
FIG. 13 illustrates a cross-sectional side elevation view of the intraosseous device of FIG. 5 during use in a second mode of operation.

Once access to the bone marrow is achieved, the user may further detach the outer penetrator hub 106 from the inner penetrator hub 108 as shown in FIG. 13, thus leaving the outer penetrator within the intraosseous space, as previously described above. Also, as previously described above, a flexible outer penetrator may be utilized so that it may be manipulated and fixed to the patient after insertion to provide a lower profile (i.e., by bending the outer penetrator down to secure it against the patient's skin).

Figure 14:
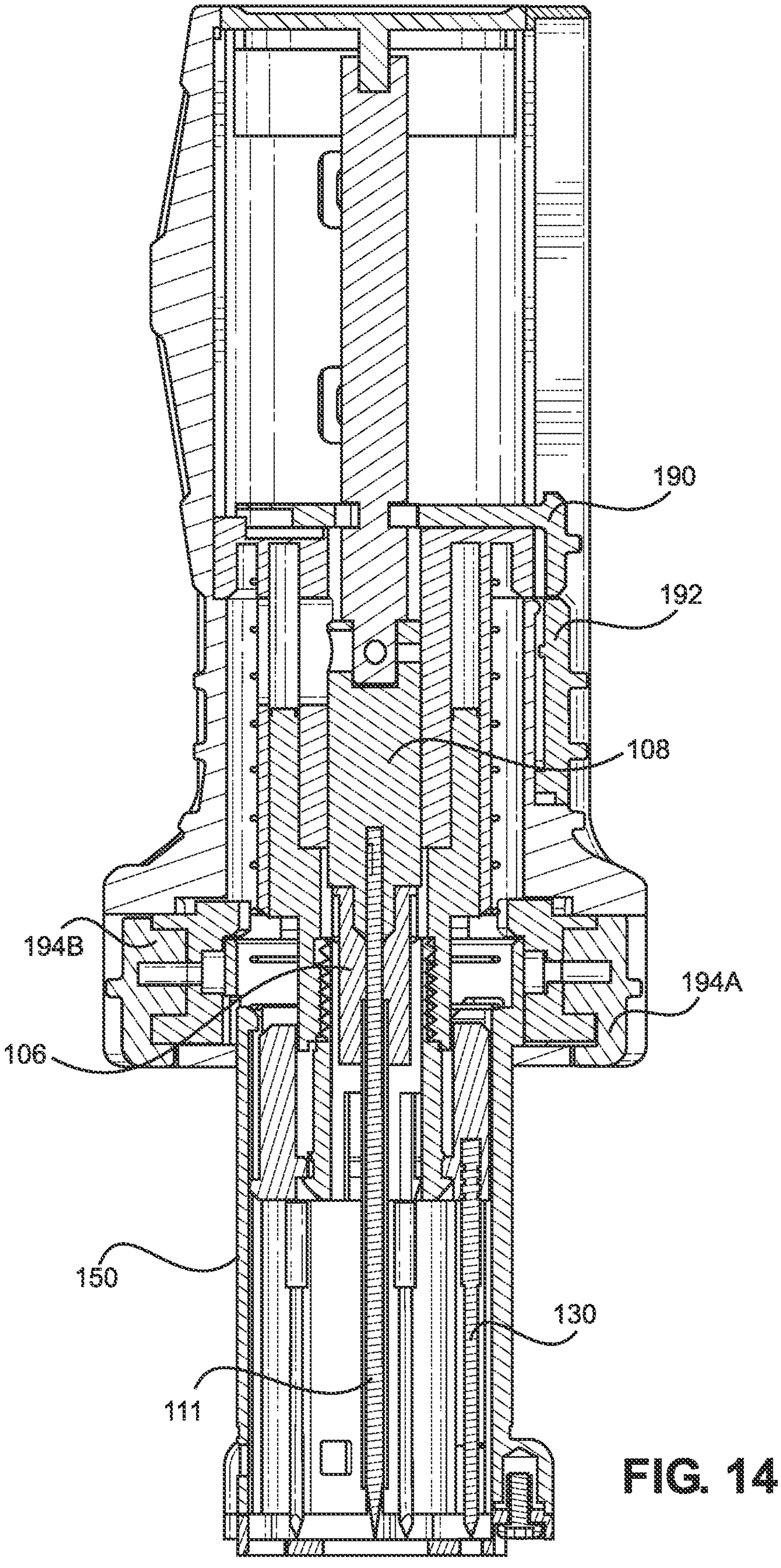
FIG. 14 illustrates a cross-sectional side elevation view of the intraosseous device of FIG. 5 during use in a second mode of operation.

Referring to FIG. 14, the protective shield 150 is shown in its first or extended position in which it is operable to provide sharps protection from the penetrator assembly. One or both of the safety buttons 194A, 194B may be pressed by the user to lock the protective shield in the extended position. Each of the safety buttons 194A, 194B has an overhang portion configured to abut the interior shoulder 157 at the proximal end of the protective shield 150 when in the extended position in order to prevent the shield from inadvertently retracting back into the internal cavity of the outer sleeve.

Figure 17:
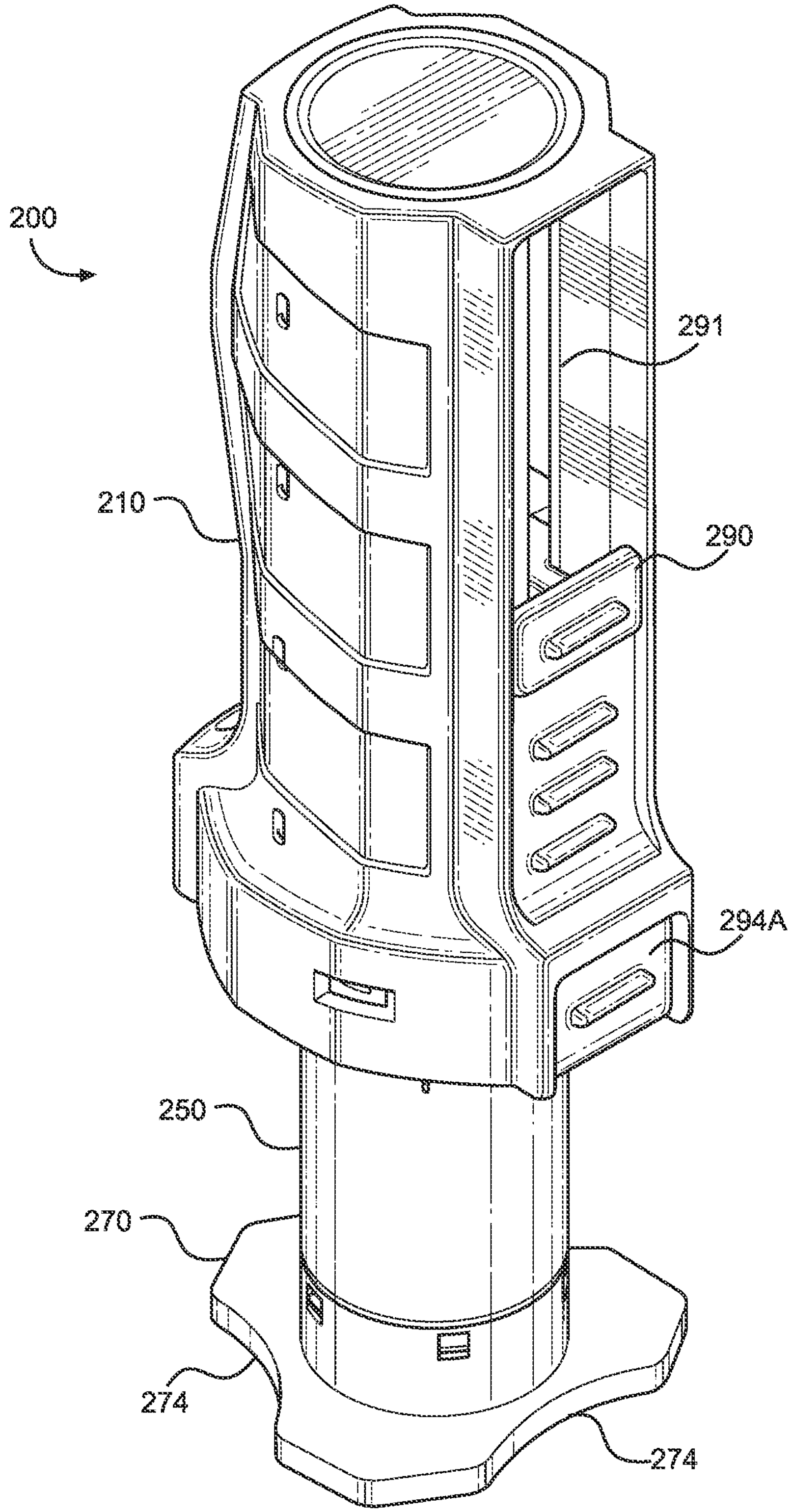
FIG. 17 illustrates a perspective view of an intraosseous access device according to another implementation of the present disclosure.
Figure 18:
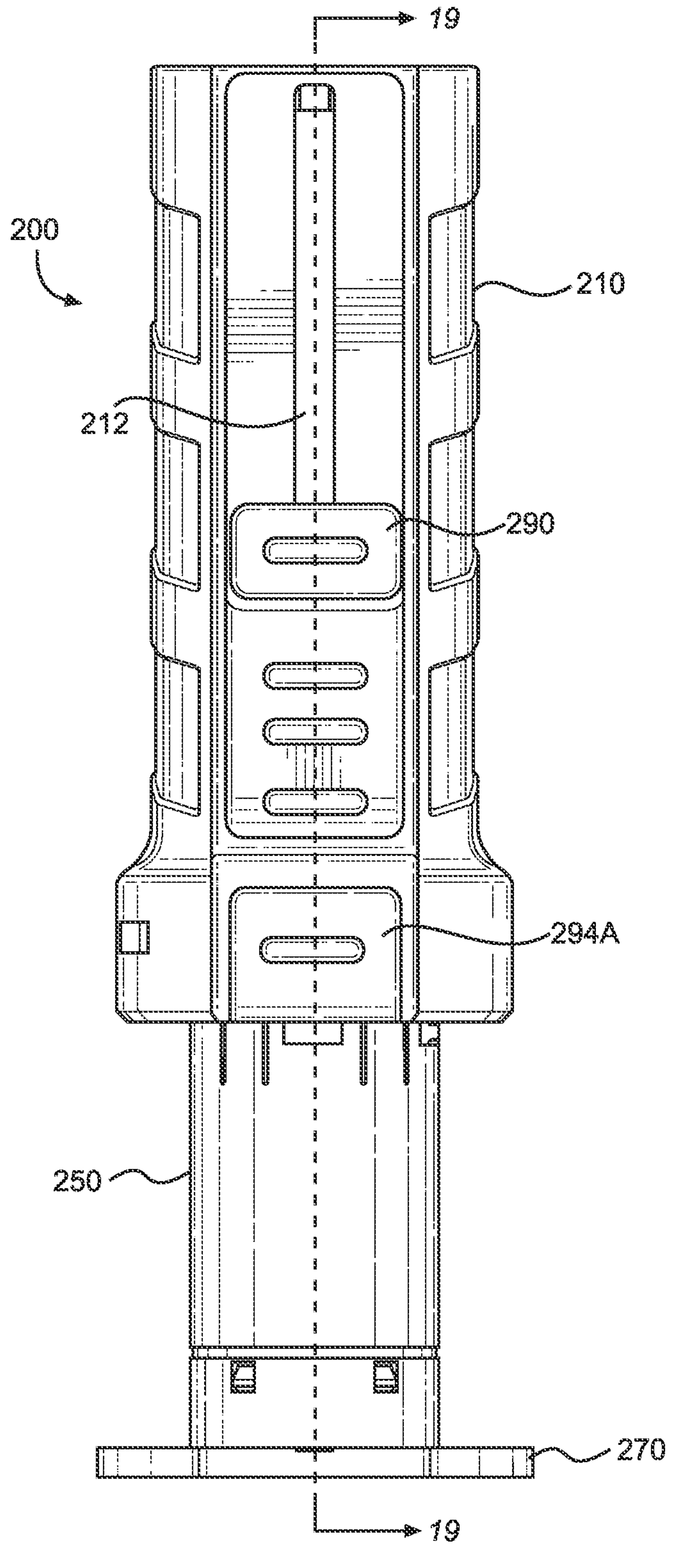
FIG. 18 illustrates a front view of the intraosseous access device of FIG. 17.

FIGS. 17 and 18 depict another implementation of an intraosseous (10) access device 200. Each implementation of the intraosseous access device may comprise one or more components and/or characteristics of the other implementations of the intraosseous access device described and depicted throughout this disclosure. In a first mode of operation, the intraosseous access device 200 is operable to help locate a suitable insertion site and manually penetrate underlying bone, such as a patient's sternum, to quickly and easily provide a conduit to an intraosseous space within the bone for associated medical procedures, including delivery of fluid and medication, aspiration, and biopsy of bone marrow, among others. In a second mode of operation, the intraosseous access device is operable for manual insertion into a patient's intraosseous space at a peripheral insertion site.

Figure 19:
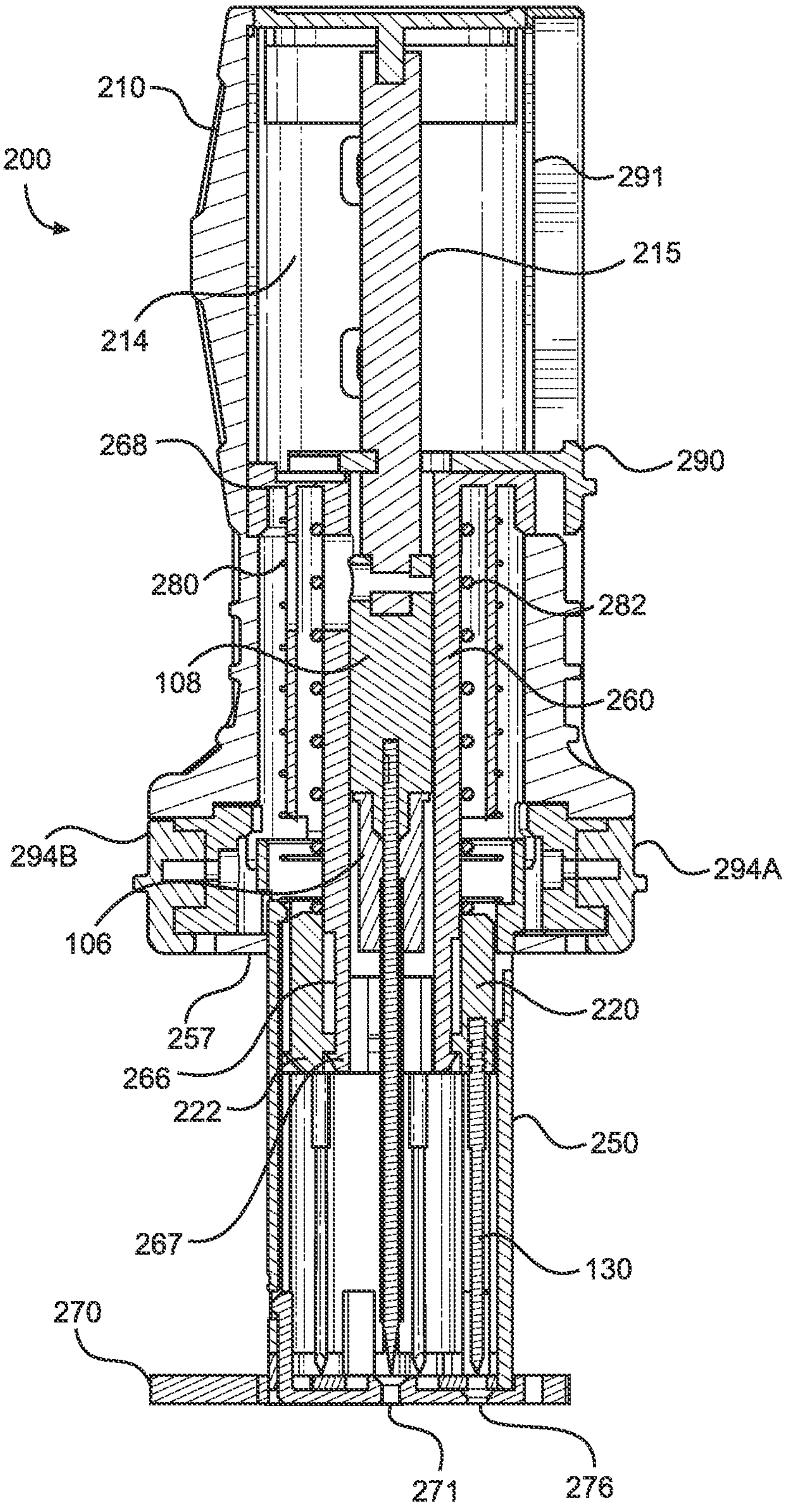
FIG. 19 illustrates a cross-sectional view of the intraosseous access device taken along line 19-19 in FIG. 18.

FIG. 19 depicts the intraosseous access device 200 of the present disclosure in an initial position, or resting state, prior to use in either the first mode of operation or the second mode of operation. The intraosseous access device 200 comprises a penetrator assembly as previously described in detail above. The intraosseous access device 200 further comprises a housing 205, a bone probe ring 220, a bone probe 130 as previously described in detail above, a protective shield 250, a retainer 260, a stabilizer base 270, a first biasing member 280, and a second biasing member 282. The housing 205 includes an outer sleeve 210 defining a handle. The handle may include a textured outer surface to provide an anti-slip grip for the user. The handle may also be ergonomically contoured to provide a comfortable grip for the user.

As previously described, the penetrator assembly comprises an inner penetrator 111, an inner penetrator hub 108, an outer penetrator 113, and an outer penetrator hub 106. A proximal end 119 of the inner penetrator hub 108 includes a recess 104 configured to receive a distal portion of a housing core 215, such as a rod or post. A proximal portion of the housing core 215 is coupled to a proximal end the housing. The housing core 215 includes a thin neck portion 224 configured to engage a slider 290 to lock the retainer 260 in a first or deployed position when the intraosseous access device 200 is in a first mode of operation for locating a sternal insertion site and manually penetrating underlying bone to quickly and easily provide a conduit to an intraosseous space within the bone. The slider 290 is configured to disengage the thin neck portion 224 of the housing core 215 to unlock the retainer 260 from its deployed position. Disengaging the slider 290 from the housing core 215 furthermore permits the user to manually slide the retainer to its undeployed position when the intraosseous access device is in a second mode of operation for manual insertion of the penetrator assembly into a patient's intraosseous space at a peripheral insertion site.

The outer sleeve 210, the bone probe ring 220, and the retainer 260 each have a generally cylindrical or tubular shaped portion. An exterior surface of the outer sleeve 210 includes a longitudinal track 291 defining a longitudinal channel configured to guide the slider 290 from a first position in which the intraosseous access device is in the first mode of operation for sternal intraosseous access, to a second position in which the intraosseous access device is in the second mode of operation for peripheral intraosseous access. The bone probe ring 220 includes a distal end having an outwardly protruding annular flange 222. The bone probe ring 220 has a generally cylindrical shape and includes a passageway configured to slidably receive a distal portion of the retainer 260.

The distal end of the bone probe ring 220 further includes a plurality of circumferentially spaced apart openings from which respective bone probes 130 extend. For instance, the distal end of the bone probe ring may include five openings corresponding to five bone probes, although other implementations may have more or less openings and corresponding bone probes. In some implementations, a single bone probe may be provided. In other implementations, a plurality of bone probes (for example, two or more bone probes, and preferably three bone probes) may be provided. The bone probes may be arranged so that they stabilize the intraosseous access device during insertion of a penetrator assembly into the intraosseous space at a desired location and orientation. For example, three bone probes may be arranged in a triangle surrounding the inner and outer penetrators.

The bone probe ring 220 is slidably disposed within the protective shield 250. The internal cavity 214 is configured to slidably receive the protective shield 250. A distal end of the retainer 260 is slidably coupled to the bone probe ring 220 and is configured to allow the bone probe ring to slidably move between a first or extended position and a second or retracted position. The retainer 260 defines a single-piece chassis and has an internal passageway 264 configured to receive the inner and outer penetrator hubs 108, 106. The proximal end of the retainer 260 includes an outwardly protruding annular flange 268. The distal end of the retainer 260 includes a plurality of resilient fingers 266 annularly disposed around a circumference of the retainer, each finger including a respective ridge or nub 267 protruding radially outward therefrom.

The protective shield 250 includes a proximal end having an annular inner shoulder 257. The first biasing member 280 is disposed between the protective shield shoulder 257 and the retainer flange 268, and the second biasing member 282 is disposed between the proximal end of the bone probe 220 and the retainer flange 268, as will be discussed in greater detail below. The protective shield 250 is operable to move between a first or extended position to provide sharps protection from the distal ends of the inner and outer penetrators 111, 113 as well as the bone probes 130, and a second or retracted position to expose the respective inner and outer penetrators 111, 113 and the bone probes 130 during an insertion procedure. The respective ridges or nubs 267 disposed on the resilient fingers 266 of the retainer 260 are configured to engage an inwardly protruding annular flange of the bone probe ring 220 to limit how far the bone probe ring and respective bone probes may extend relative to the retainer and the protective shield. The distal end of the bone probe ring may comprise a radially outward protruding annular flange configured to engage the annular shoulder 257 of the protective shield 250 to limit how far the protective shield may extend from the outer sleeve 210 when the shield is in the first or extended position. When the protective shield 250 is in the first or extended position, the tips 132 of each bone probe 130 are disposed within the interior space of the shield to provide sharps protection. When the protective shield is in a second or retracted position, the tips 132 of each bone probe 130 extend from the distal end of the shield.

A stabilizer base 270 is connected to the telescoping shield 250. The base 270 comprises a guide hole 271 configured to guide the penetrator assembly during an insertion procedure. The base 270 also comprises a plurality of through-holes 276 corresponding to, and aligned with, the bone probes. The through-holes 276 are configured to permit passage of the respective bone probes through the stabilizer base 270 during an insertion procedure. The base 270 may also comprise an alignment feature 274, such as an arc-shaped cutout portion of the base. The alignment cutout 274 is configured to approximate the shape of the sternal notch of a human patient and is operable to indicate proper placement of the base 270 against the patient. The intraosseous access device 100 is properly located on the chest of a patient when the base 270 is placed over the sternum, for instance during the first mode of operation, such that the sternal notch is visible and at least partially (and, preferably, completely) bounded by the alignment cutout 274

The intraosseous access device 200 may also include the safety latch 140 as previously described above to prevent the intraosseous access device from moving from the first or extended position to the second or retracted position. In particular, the safety latch 140 includes a first end 142 configured to engage the outer sleeve 210. Further, the safety latch 140 includes a second end 143 configured to prevent the protective shield 250 from moving to its second or retracted position. The first end 142 of the latch 140 includes a pin portion 145 configured to be inserted within the longitudinal track 291 to engage the side channel in the outer sleeve to block the slider 190 from sliding from a first position to a second position. The second end 143 of the latch 140 is configured to depress a safety button 294A to prevent the shield 250 from telescopically retracting into the outer sleeve 210 toward its second or retracted position in order to maintain sharps protection of the penetrator assembly and the bone probes. A user may remove the safety latch 140 from the intraosseous access device 200 by pulling a tab 144 to disengage the pin 145 from the side channel of the outer sleeve 210, thus allowing the slider 290 to be actuated to manually retract the telescoping protective shield 250. Removal of the safety latch also stops the first safety button 294A from being pressed so as to unlock the protective shield 250 from its extended position.

Also, as previously described, the intraosseous access device 200 may be used in a first mode of operation to help locate a suitable insertion site and manually penetrate underlying bone, such as a patient's sternum, for quickly and easily providing a conduit to an intraosseous space within the bone. Prior to use, in an initial position of the first mode of operation, the protective shield 250 is in its first or extended position, as shown in FIG. 19. In operation, the user first must remove the safety latch 140 from the intraosseous access device by pulling on the tab 144, thereby disengaging the pin 145 at the first end 142 from the side channel of the outer sleeve 210 before the intraosseous access device can be used in an intraosseous insertion procedure. The pin prevents operation of the intraosseous access device when inserted into the channel by blocking the shield 250 from telescopically retracting into the outer sleeve 250. The locking pin may be inserted during manufacture or before use of intraosseous access device, and removed to prepare the intraosseous access device for use.

The intraosseous access device 200 may be operated by placing the stabilizer base 270 against the skin of a patient over a bone, such as the sternum, into which it is desired to insert the penetrator assembly. The base 270 has an arc-shaped alignment cutout 274 that helps the user align the intraosseous access device with a patient's sternal notch. In other implementations, guide features may be provided to facilitate alignment with anatomical landmarks at other infusion sites. Once the stabilizer base 270 is aligned with and placed against the insertion site, the user operates the intraosseous access device by pushing down on the handle 210. As the handle 110 is pushed, the protective shield 250 telescopically retracts into the internal cavity 214 of the outer sleeve to move from its first or extended position to its second or retracted position. The first biasing member 280 is disposed between the flange 268 at the proximal end of the retainer 260 and the shoulder 257 at the proximal end of the protective shield 250. The first biasing member 280, such as a compression spring, is operable to bias the protective shield toward its extended position. The protective shield thus moves against the biasing force of the first biasing member 280 as it is retracted into the internal cavity of the outer sleeve. As the shield 250 telescopically retracts into the outer sleeve 210, the penetrator assembly 111, 113, as well as the surrounding bone probes 130, protrude from the stabilizer base 270 to penetrate the patient's skin and underlying soft tissue. The stabilizer base 270 assists in keeping the intraosseous access device 200 over the desired insertion site and in the desired orientation. During use, the base 270 is substantially perpendicular to the penetrator assembly and assists in introducing the inner and outer penetrators 111, 113 straight into the patient's sternum.

Figure 20:
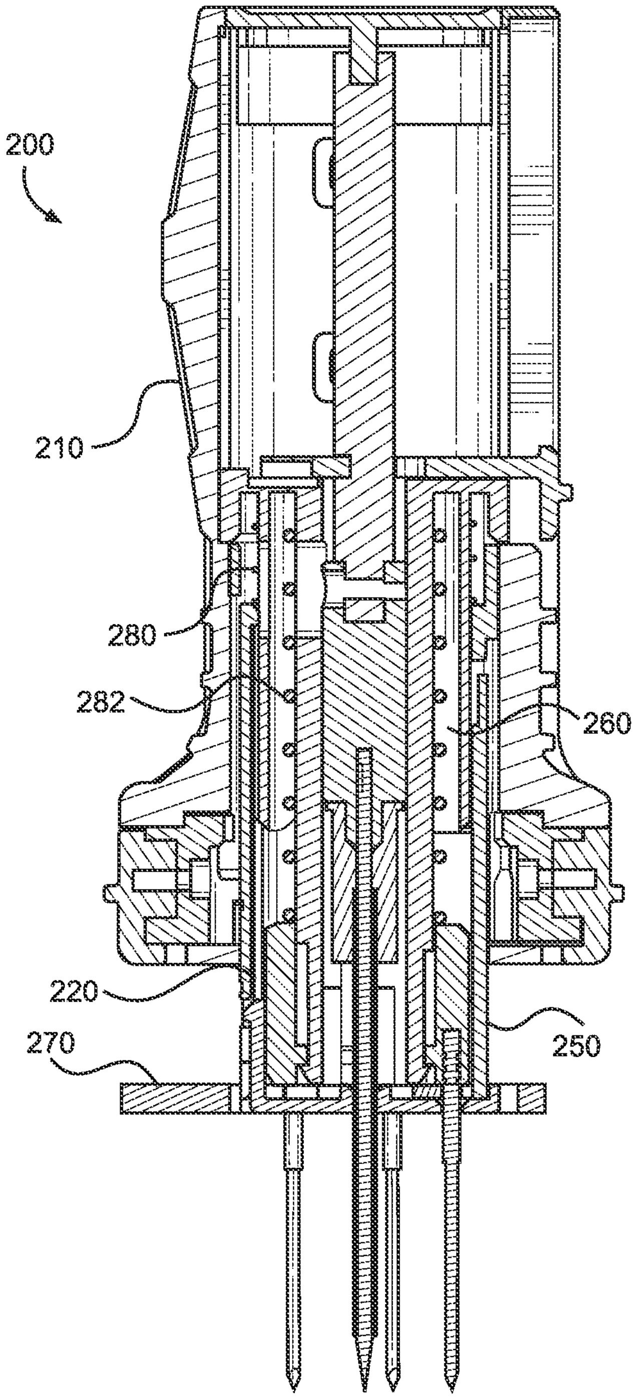
FIG. 20 illustrates a cross-sectional side elevation view of the intraosseous access device of FIG. 19 during use in a first mode of operation.

A first depth of insertion of the inner and outer penetrators 111, 113 is determined when the tips 132 of the respective bone probes 130 contact the bone. At this first depth of insertion, the inner and outer penetrators 111, 113 are inserted the same distance as the bone probes 130, as depicted in FIG. 20, and therefore the inner and outer penetrators do not yet penetrate into the intraosseous space.

Figure 21:
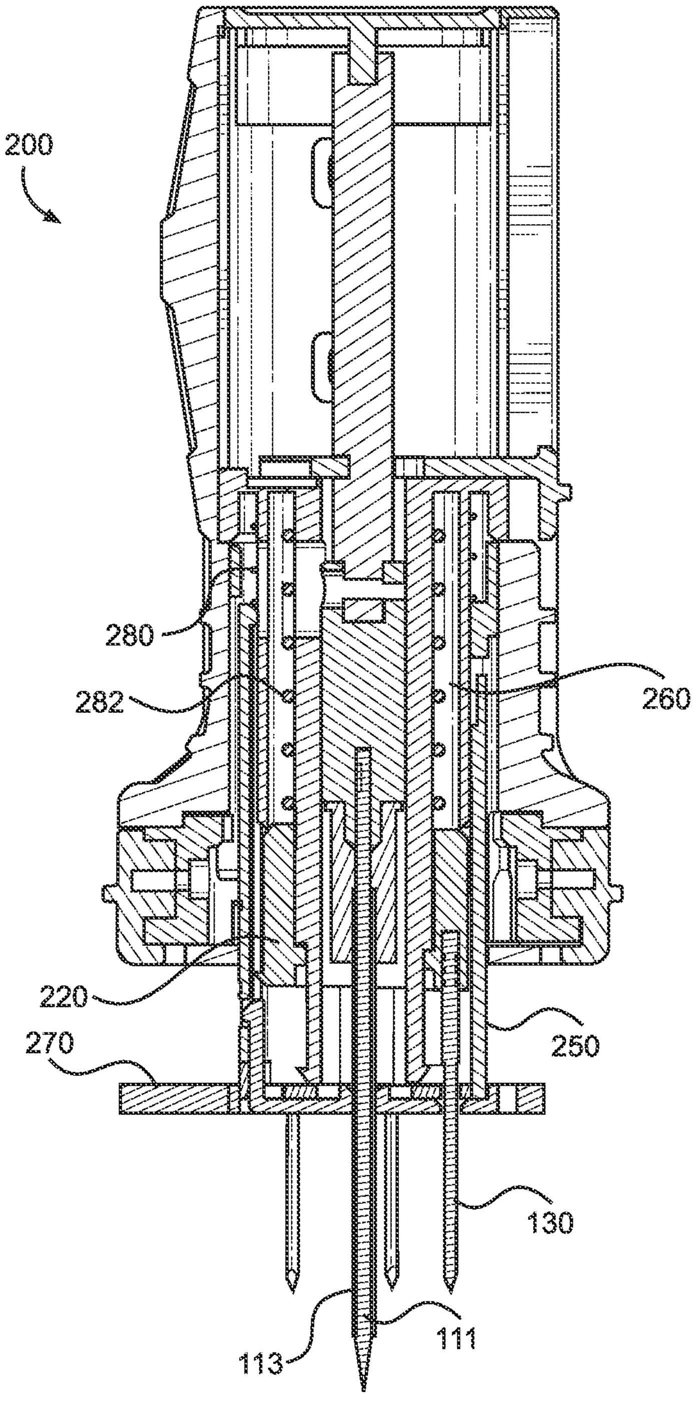
FIG. 21 illustrates a cross-sectional side elevation view of the intraosseous access device of FIG. 19 during use in a first mode of operation.

Insertion of the inner and outer penetrators 111, 113 to a second depth of insertion (e.g., into the intraosseous space) is then carried out by the user pushing the handle 210 again to continue retracting the protective shield 250 into the outer sleeve 210, such that a surface of the base 270 may contact the bone probe ring 220 to correspondingly slide the bone probe ring 220 and the associated bone probes 130 into the cavity 214 of the outer sleeve 210, as shown in FIG. 21. Such retraction of the bone probe ring into the outer sleeve is moreover a result of further penetration of the penetrator assembly into the intraosseous space while the force applied by the bone probes to the anterior cortex of the bone causes the bone probe ring to slide upward to its retracted position. In other words, the protective shield 250 is moved from its first or extended position to its second or retracted position to deploy the inner and outer penetrators 111, 113 into the intraosseous space.

The second biasing member 282 is disposed between the flange 268 at the proximal end of the retainer 260 and the proximal end of the bone probe ring 220. The second biasing member 282, such as a compression spring, is operable to bias the bone probe ring and is corresponding bone probes toward an extended position. The bone probe ring therefore is urged against the biasing force of the second biasing member 282 as it is retracted into the internal cavity of the outer sleeve. The biasing force applied to the bone probe ring by the second biasing member 282 ensures that the respective bone probes are remain properly set against the anterior cortex of the bone before the penetrator assembly is advanced into the intraosseous space. Moreover, the retainer 260 and the outer sleeve 210 are rotatable relative to the bone probe ring 220. Thus, the user may also rotate the handle while pushing it in order to facilitate penetration of the penetrator assembly into the bone without disturbing the position of the bone probe ring or the placement of the bone probes inserted into the skin and underlying tissue.

As the bone probe ring 220 slides into the cavity of the outer sleeve 210, an internal annular flange 225 of the bone probe ring 220 no longer abuts the corresponding ridges or nubs 267 protruding outwardly from the distal end of the retainer 260. The bone probe ring 220 is operable to be retracted into the cavity of the outer sleeve until a proximal end of the bone probe ring abuts an annular overhang portion of the retainer 260, or until the internal annular flange 225 abuts a shoulder portion of the retainer.

Figure 22:
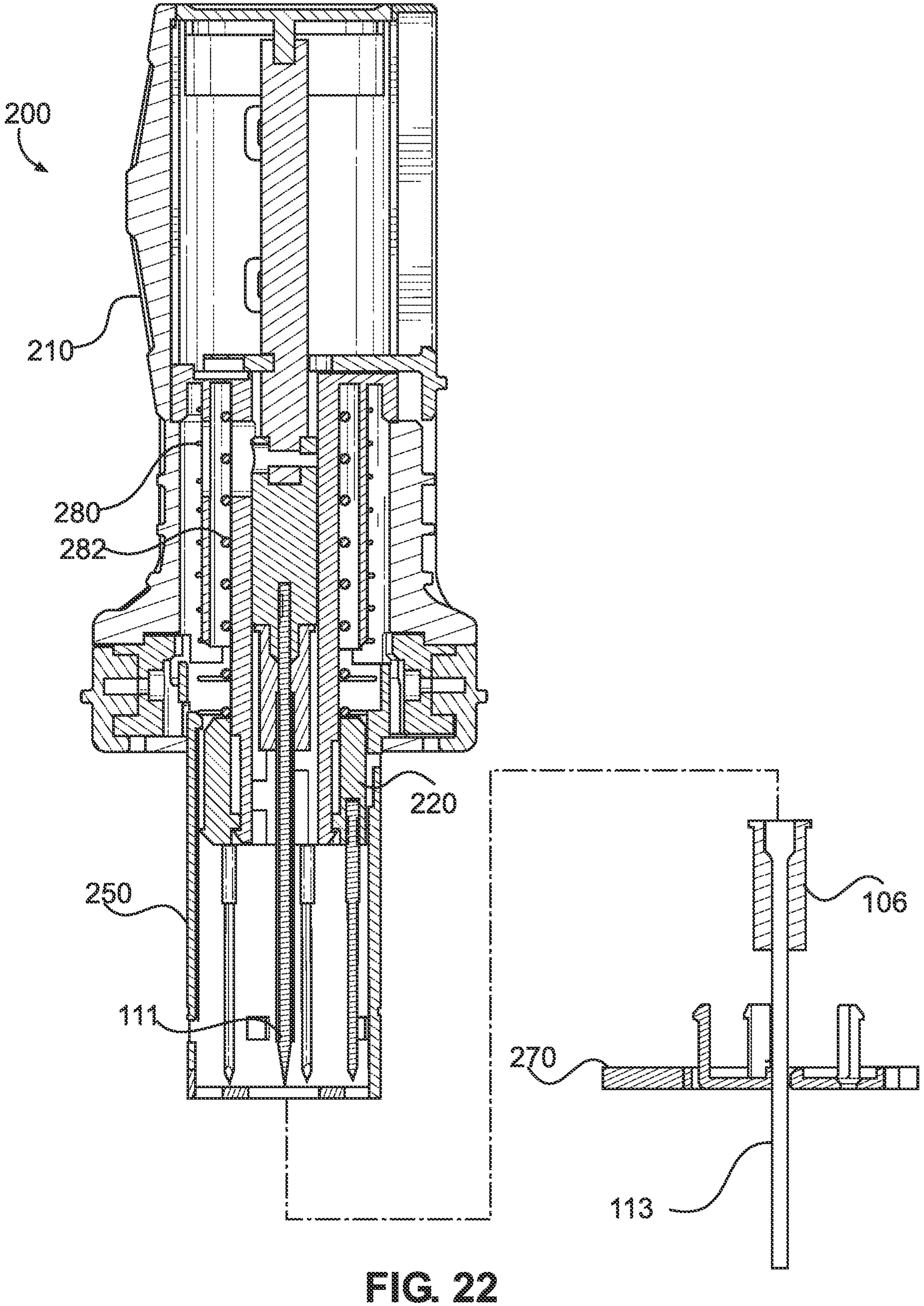
FIG. 22 illustrates a cross-sectional side elevation view of the intraosseous access device of FIG. 19 during use in a first mode of operation.

As shown in FIG. 22, once the inner and outer penetrators 111, 113 have penetrated the patient's bone to a desired depth, a release mechanism uncouples the base 270 from the protective shield 250. For instance, the retainer may be configured to allow the bone probe ring to slide approximately 10 millimeters, such that the depth of insertion of the penetrator assembly into the bone is likewise approximately 10 millimeters. The release mechanism may include one or more flexible latches on the stabilizer base each configured to releasably engage a corresponding catch at the distal end of the protective shield. The outer penetrator hub 106 is also uncoupled from the inner penetrator hub 108 (and thus the outer penetrator 113 is likewise uncoupled from the inner penetrator 111). The depth of penetration is preferably set so that the insertion of the inner and outer penetrators 111, 113 will stop when their tips are in the patient's bone marrow. After the release mechanism is triggered, the remainder of the intraosseous access device 200 may be withdrawn from the insertion site to leave in place the stabilizer base 270, the outer penetrator hub 106, and the outer penetrator 113 at the insertion site.

As the handle of the intraosseous access device is lifted away from the insertion site, the first biasing member 280 is operable to return the protective shield 250 back to its extended position from its retracted position. In particular, as previously described, the first biasing member 280, such as a compression spring, is disposed between a flange at the proximal end of the retainer 260 and a shoulder 257 at the proximal end of the protective shield 250. The first biasing member 280 thus urges the protective shield back to its first or extended position in order to provide sharps protection for the inner penetrator tip 102 as well as the bone probe tips upon their removal from the insertion site. The second biasing member 282, such as a compression spring, is disposed in an annular space of the retainer 260, and more particularly, between the flange 268 at the proximal end of the retainer 260 and a proximal end of the bone probe assembly 220 to urge the bone probe assembly back to its extended position after an insertion procedure.

Thus, removal of the intraosseous access device 200 from the insertion site automatically moves the telescoping protective shield 250 from its second or retracted position within the internal cavity of the outer sleeve back to its first or extended position so as to protect any users from inadvertent contact with the bone probes 130 and the sharp inner penetrator tip. After the protective shield 250 is urged back to its extended position by the first biasing member 280, and the bone probe ring 220 is similarly urged back to its extended position by the second biasing member 282, the user may depress a pair of safety buttons 294A, 294B that are operable to lock the protective shield in the extended position. Each of the safety buttons 294A, 294B has an overhang portion configured to abut the annular inner shoulder 257 of the protective shield 250 when in the extended position in order to block the shield from telescopically retracting back into the internal cavity of the outer sleeve.

In some implementations, the base 270 may be adhered to the patient's skin to protect the infusion site and to provide an anchor for strain relief for any tubing that may be coupled to the infusion tube assembly, or to provide strain relief for other tubing systems, catheters, or the like. Further, a flexible outer penetrator may be utilized so that it may be manipulated and fixed to the patient after the stabilizer assembly is removed in order to provide a lower profile (i.e., by bending the outer penetrator down to secure it against the skin).

Figure 23:
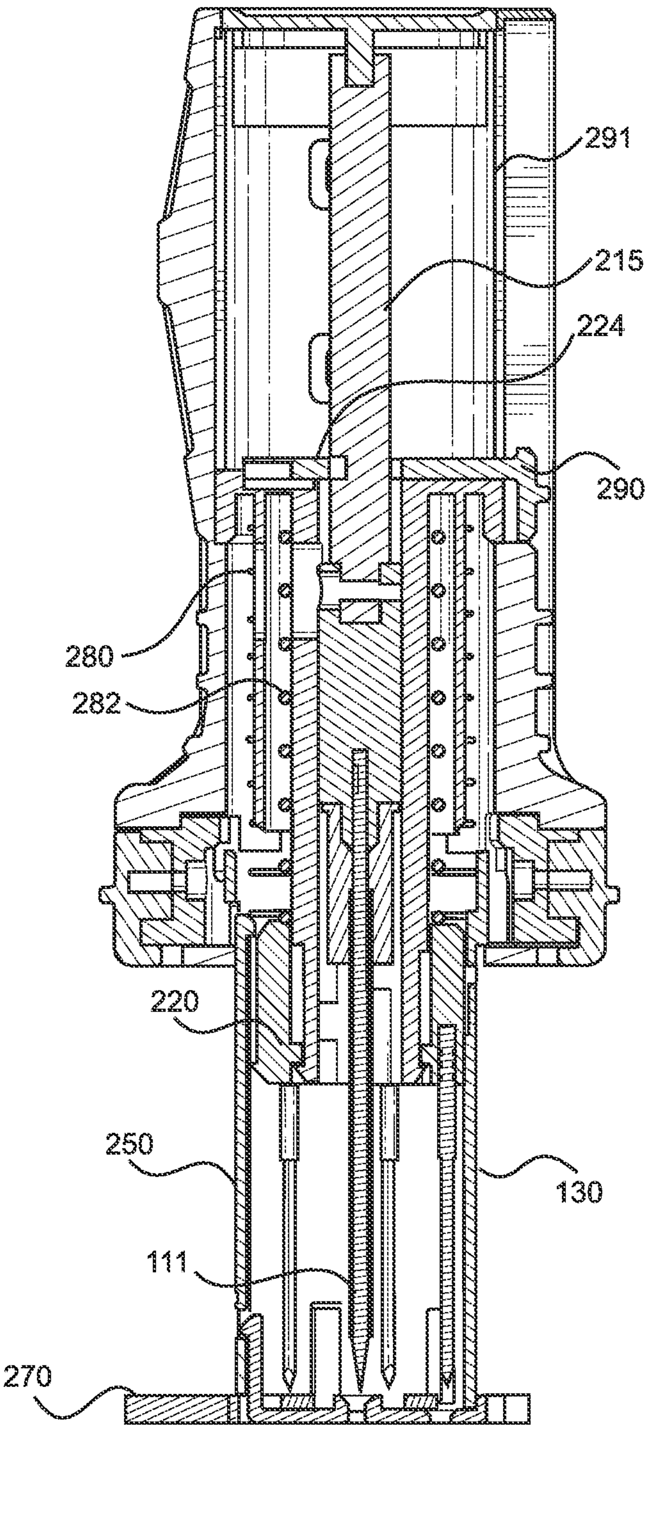
FIG. 23 illustrates a cross-sectional side elevation view of the intraosseous access device of FIG. 19 during use in a second mode of operation.
Figure 24:
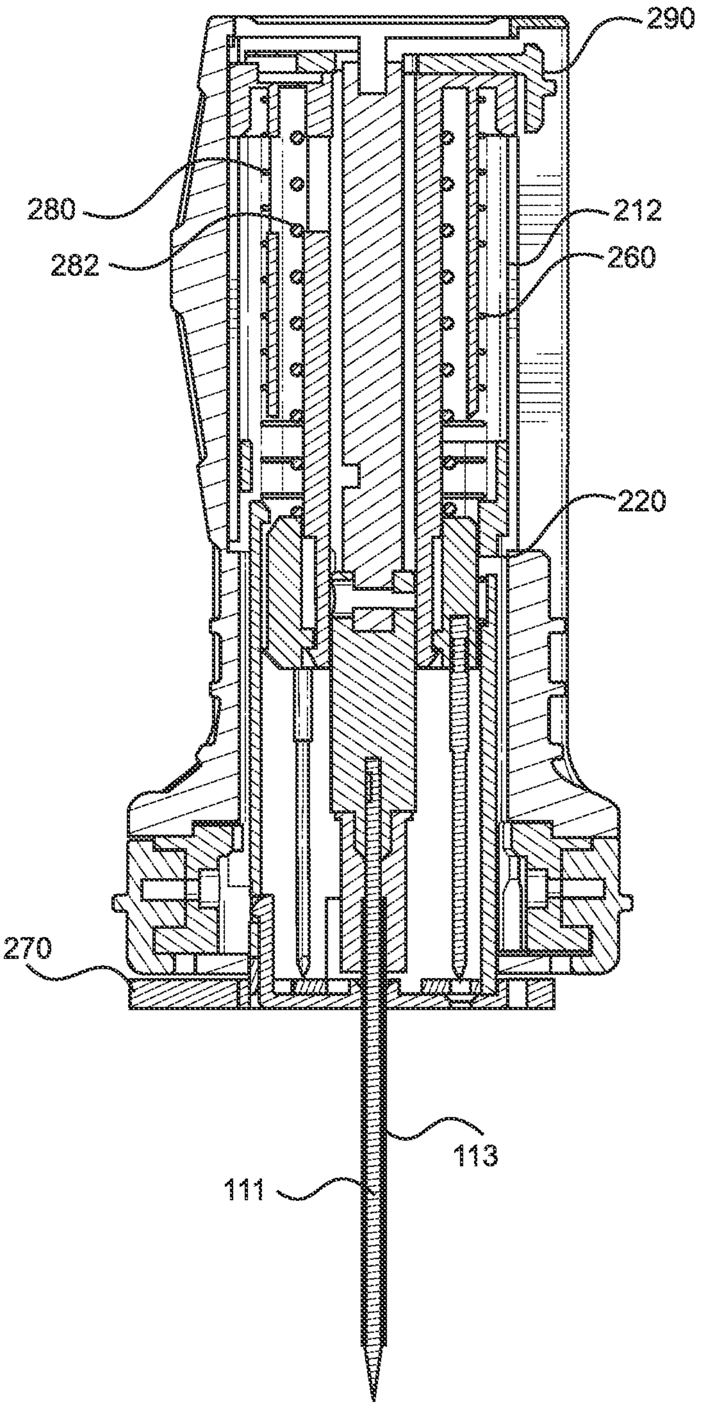
FIG. 24 illustrates a cross-sectional side elevation view of the intraosseous access device of FIG. 19 during use in a second mode of operation.

In a second mode of operation, the intraosseous access device 200 is operable for manual insertion into a patient's intraosseous space at a peripheral insertion site. Prior to use, in an initial position of the second mode of operation, both the outer sleeve 210 and the protective shield 250 are in their respective first or extended positions, as shown in FIG. 23. In this second mode of operation, the user is able to manually retract the protective shield 250 prior to intraosseous insertion so that the penetrator assembly can be manually driven into an intraosseous space at a peripheral insertion site. For example, in the second mode of operation, the user first must remove the safety latch 240 in the same manner as described above with regard to the first mode of operation. Next, the user presses the slider 290 inwardly to align the slider aperture with the neck 224 of the housing core 215, such that the user can then manually move the slider 290 toward the proximal end of the housing to correspondingly slide the retainer 260, the bone probe ring 220, and the protective shield 250 together to a retracted position into the internal cavity of the outer sleeve 210, as shown in FIG. 24. Consequently, the inner and outer penetrators 111, 113 protrude from the retracted stabilizer base 270 so that the user can manually insert the penetrator assembly into an intraosseous space by applying force and twisting or rotating the handle 210 back and forth. Accordingly, the retainer 260, the bone probe ring 220 with bone probes 103, and the protective shield 250 are manually retracted upward relative to and inside the handle without applying any force to the first and second biasing members 280, 282 (i.e., without compressing the respective compression springs).

Figure 25:
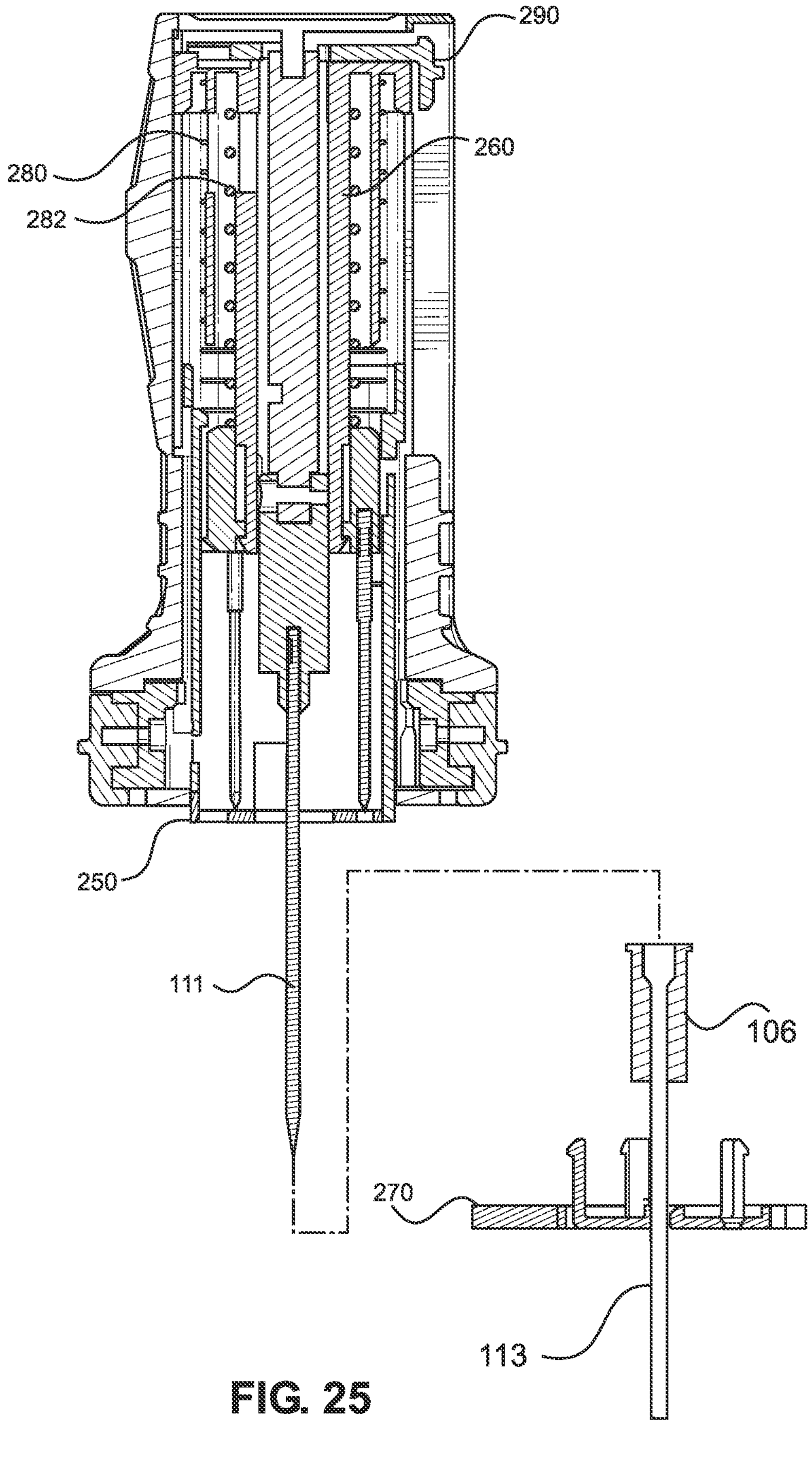
FIG. 25 illustrates a cross-sectional side elevation view of the intraosseous access device of FIG. 19 during use in a second mode of operation.

Thus, in the second mode of operation, the manual intraosseous access device 200 may be used for insertion of the inner and outer penetrators 111, 113 into an intraosseous space at a peripheral insertion site. Once access to the bone marrow is achieved, the user may further detach the outer penetrator hub 106 from the inner penetrator hub 108 as shown in FIG. 25, thus leaving the outer penetrator within the intraosseous space, as previously described above. The outer penetrator may be a flexible cannula so that it may be manipulated and fixed to the patient after insertion to provide a lower profile (i.e., by bending the outer penetrator down to secure it against the patient's skin).

Figure 26:
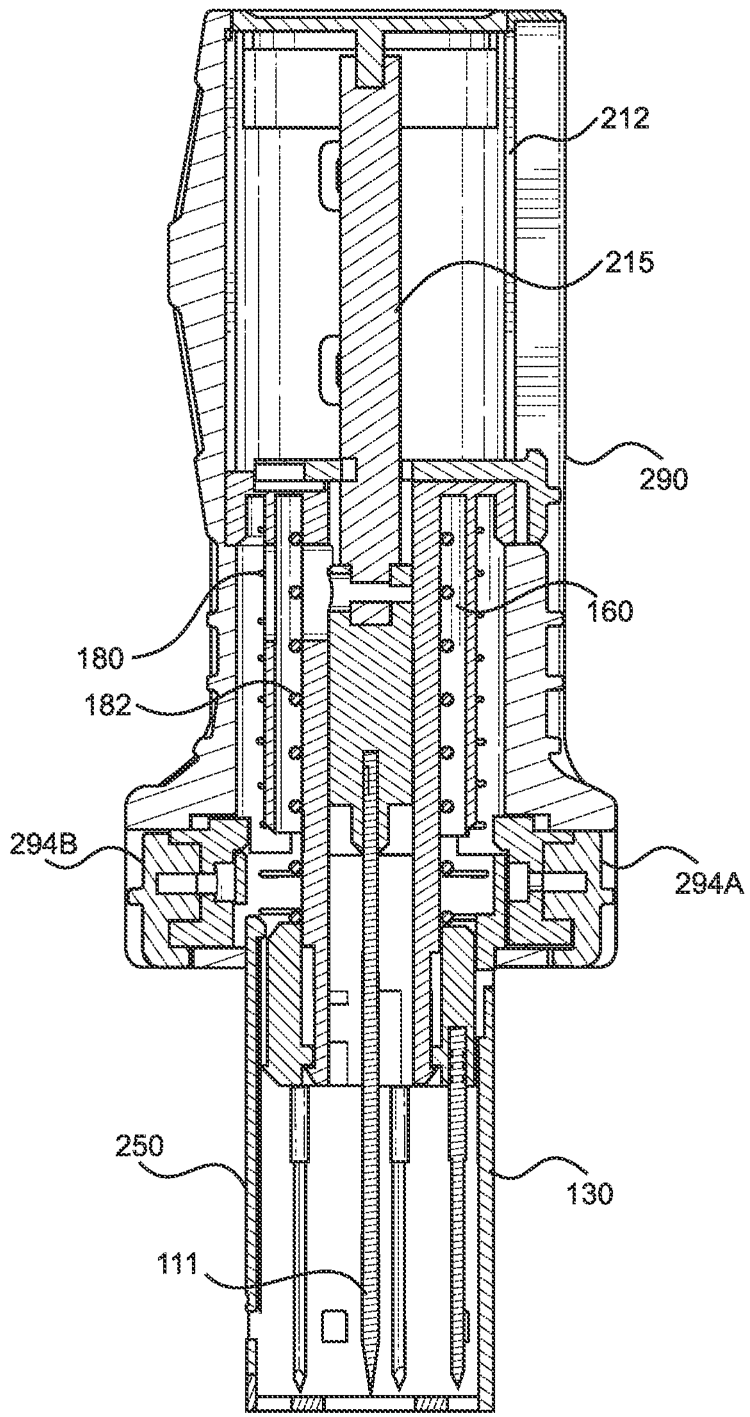
FIG. 26 illustrates a cross-sectional side elevation view of the intraosseous access device of FIG. 19 during use in a second mode of operation.

Referring to FIG. 26, the protective shield 250 is shown moved back to its first or extended position in which it is operable to provide sharps protection from the sharp penetrator assembly and bone probes. One or both of the safety buttons 294A, 294B may be pressed by the user to lock the protective shield in the extended position. Each of the safety buttons 294A, 294B has an overhang portion configured to abut the inwardly protruding shoulder 257 at the proximal end of the protective shield 250 when in the extended position in order to prevent the shield from inadvertently retracting back into the internal cavity of the outer sleeve.

While the intraosseous access device has been described in terms of what may be considered to be specific aspects, the present disclosure is not limited to the disclosed aspects. Moreover, the many features and advantages of the disclosure are apparent from the detailed specification, and thus, it is intended by the appended claims to cover all such features and advantages of the disclosure which fall within the spirit and scope of the disclosure. Further, it is not desired to limit the disclosure to the exact construction and operation illustrated and described, and accordingly, all suitable modifications and equivalents may be resorted to, falling within the scope of the disclosure. Accordingly, the present disclosure should be considered as illustrative and not restrictive. As such, this disclosure is intended to cover various modifications and similar arrangements included within the spirit and scope of the claims, which should be accorded their broadest interpretation so as to encompass all such modifications and similar structures.

What is claimed is:

1. An intraosseous access device for accessing an intraosseous space, the intraosseous access device comprising:

a penetrator assembly having a sharp penetrating end operable to penetrate a bone and associated bone marrow;

a housing having an internal cavity and an outer sleeve, the outer sleeve defining a handle operable to manually drive the penetrator assembly into the bone and associated bone marrow;

a retainer having a distal retainer end and a proximal retainer end, the retainer slidably coupled to the outer sleeve; and a protective shield having a distal shield end, a proximal shield end, and a longitudinal hollow passageway extending between the distal shield end and the proximal shield end, the protective shield slidably coupled to the outer sleeve;

where the penetrator assembly is operable to provide intraosseous access to the intraosseous space at a sternal insertion site by manually driving the penetrator assembly into the intraosseous space when the intraosseous access device is in a first mode of operation in which the retainer is locked in a deployed position; and where the penetrator assembly is operable to provide intraosseous access to the intraosseous space at a peripheral insertion site by manually driving the penetrator assembly into the intraosseous space when the intraosseous access device is in a second mode of operation in which the retainer is unlocked from the deployed position and manually slid in a proximal direction relative to the outer sleeve into the internal cavity of the housing to an undeployed position.

2. The intraosseous access device according to claim 1, wherein the penetrator assembly further comprises an inner penetrator hub having a distal end and a proximal end, an inner penetrator extending from the distal end of the inner penetrator hub, an outer penetrator hub having a distal end and a proximal end, and an outer penetrator extending from the distal end of the outer penetrator hub, the outer penetrator defining a longitudinal hollow bore configured to slidably receive the inner penetrator.

3. The intraosseous access device according to claim 2, wherein the proximal end of the outer penetrator hub is releasably engaged to the distal end of the inner penetrator hub.

4. The intraosseous access device according to claim 2, further comprising a housing core fixedly disposed within the internal cavity of the housing, the housing core including a distal core end coupled to the proximal end of the inner penetrator hub.

5. The intraosseous access device according to claim 2, wherein the inner penetrator comprises a rigid stylet, and the outer penetrator comprises a flexible cannula.

6. The intraosseous access device according to claim 1, wherein the handle includes an ergonomic grip suitable for grasping during the first and second modes of operation.

7. The intraosseous access device according to claim 1, wherein the handle is configured to allow manual force to be applied and at the same time permit rotation of the handle to rotate the penetrator assembly during intraosseous insertion of the penetrator assembly during the second mode of operation by manually pushing and twisting the handle.

8. The intraosseous access device according to claim 1, wherein the protective shield is configured to move between an extended position and a retracted position relative to the outer sleeve and the retainer during the first mode of operation.

9. The intraosseous access device according to claim 8, wherein the protective shield is configured to provide sharps protection from the sharp penetrating end of the penetrator assembly when the protective shield is in the extended position during the first mode of operation, and wherein the protective shield is configured to expose the sharp penetrating end of the penetrator assembly when the protective shield is in the retracted position to permit insertion of the penetrator assembly into the bone and associated bone marrow during the first mode of operation.

10. The intraosseous access device according to claim 9, further comprising a first biasing member disposed between the retainer and the protective shield, the first biasing member configured to bias the protective shield toward the extended position during the first mode of operation.

11. The intraosseous access device according to claim 8, further comprising a bone probe ring slidably coupled to the retainer, the bone probe ring having a distal ring end and a proximal ring end; and a bone probe extending from the distal ring end of the bone probe ring, the bone probe including a bone probe tip operable to penetrate skin and subcutaneous tissue.

12. The intraosseous access device according to claim 11, wherein the bone probe ring is configured to move between a first position and a second position during the first mode of operation, where the bone probe ring is closer to the distal retainer end of the retainer when the bone probe ring is in the first position than when the bone probe ring is in the second position.

13. The intraosseous access device according to claim 12, wherein the distal ring end of the bone probe ring includes an inwardly protruding nub, the nub configured to engage a first detent on the retainer to maintain the bone probe ring in the first position during the first mode of operation, and the nub configured to engage a second detent on the retainer to maintain the bone probe ring in the second position during the first mode of operation.

14. The intraosseous access device according to claim 12, further comprising a second biasing member disposed between the retainer and the bone probe ring, the second biasing member configured to bias the bone probe ring toward the first position during the first mode of operation.

15. The intraosseous access device according to claim 1, wherein the outer sleeve further comprises a longitudinal track and a slider slidably coupled to the longitudinal track, the slider operable to move the retainer and the protective shield between the deployed position and the undeployed position relative to the outer sleeve during the second mode of operation.

* * * * *